(12) United States Patent
Saba et al.

(10) Patent No.: US 6,423,527 B1
(45) Date of Patent: Jul. 23, 2002

(54) SPHINGOSINE-1-PHOSPHATE LYASE POLYPEPTIDES, POLYNUCLEOTIDES AND MODULATING AGENTS AND METHODS OF USE THEREFOR

(75) Inventors: Julie D. Saba, Emeryville; Jianhui Zhou, Redwood City, both of CA (US)

(73) Assignee: Children's Hospital Medical Center of Northern California, Oakland, CA (US)

( * ) Notice: Subject to any disclaimer, the term of this patent is extended or adjusted under 35 U.S.C. 154(b) by 0 days.

(21) Appl. No.: 08/939,309

(22) Filed: Sep. 29, 1997

(51) Int. Cl.[7] .......................... C12N 9/88; C12N 15/00; C12N 5/00; C12Q 1/68
(52) U.S. Cl. .................... 435/232; 435/320.1; 435/325; 435/6; 536/23.1; 536/23.2; 536/23.5
(58) Field of Search ................................ 435/232, 69.1, 435/320.1, 325, 6; 536/23.1, 23.2, 23.5

(56) References Cited

U.S. PATENT DOCUMENTS 5,430,169 A   7/1995   Boumendjel et al. ....... 558/169

FOREIGN PATENT DOCUMENTS

WO      WO 93/19760      10/1993

OTHER PUBLICATIONS

Marra, M. et al., GenBank Database, Accession No. WO8172, Sep. 5, 1996.*
Hillier, L. et al., GenBank Database, Accession No. T86263, Mar. 1995.*
Fulton, L., GenBank Database, Accession, No. U51031, Mar. 23, 1996.*
Amann et al., Gene, vol. 69, pp. 301–315, 1988.*
Sadahira et al., "Sphingosine 1–phosphate, a specific endogenous signaing molecule controlling cell motility and tumor cell invasiveness," *Proc. Natl. Acad. Sci.* USA 89: 9686–9690, 1992.
Veldhoven and Mannaerts, Advances in Lipid Research Vol. 26: Sphingolipids Part B: *Regulation and Function of Metabolism*, Academic Press, Inc., San Diego, 1993, pp. 69–98.

Database EMEST1 EMBL Database Accession No. AA589412, Sep. 18, 1997.
Database EMEST12 EMBL Database Accession No. T86263, Mar. 30, 1995.
Database EMEST17 EMBL Database Accession No. AA338781, Apr. 18, 1997.
Database EMEST20 EMBL Database Accession No. AA107456, Nov. 6, 1996.
Qie et al., "Identification of a *Saccharomyces* Gene, LCB3, Necessary for Incorporation of Exogenous Long Chain Bases into Sphingolipids," *The Journal of Biological Chemistry* 272(26): 16110–16117, 1997.
Saba et al., "The BSTI Gene of *Saccharomyces cervisiae* Is the Sphingosine–1–phosphate Lyase," *The Journal of Biological Chemistry* 272(42): 26087–26090, 1997.
Spiegel et al., "Sphingosine–1–phosphate, a novel second messenger involved in cell growth regulation and signal transduction, affects growth and invasiveness of human breast cancer cells," *Breast Cancer Research and Treatment* 31: 337–348, 1994.
Zhou and Saba, "Identification of the First Mammalian Sphingosine Phosphate Lyase Gene and Its Functional Expression in Yeast," *Biochemical And Biophysical Research Communications* 242: 502–507, 1998.

* cited by examiner

*Primary Examiner*—Ponnathapu Achutamurthy
*Assistant Examiner*—Peter P. Tung
(74) *Attorney, Agent, or Firm*—Seed IP Law Group PLLC

(57) ABSTRACT

Compositions, methods and kits for diagnosing and treating cancer are provided. Therapeutic compositions may comprise agents that modulate the expression or activity of a springiness-1-phosphate lease (SPL). Such compositions may be administered to a mammal afflicted with cancer. Diagnostic methods and kits may employ an agent suitable for detecting alterations in endogenous SPL. Such methods and kits may be used to detect the presence of a cancer or to evaluate the prognosis of a known disease. SPL polypeptides, polynucleotides and antibodies are also provided.

7 Claims, 20 Drawing Sheets

Fig. 1A

| | |
|---|---|
| ATG AGT GGA GTA TCA AAT AAA ACA GTA TCA ATT AAT GGT TGG TAT GGC<br>Met Ser Gly Val Ser Asn Lys Thr Val Ser Ile Asn Gly Trp Tyr Gly<br>1              5                    10                  15 | 48 |
| ATG CCA ATT CAT TTA CTA AGG GAA GAA GGC GAC TTT GCC CAG TTT ATG<br>Met Pro Ile His Leu Leu Arg Glu Glu Gly Asp Phe Ala Gln Phe Met<br>               20                      25                    30 | 96 |
| ATT CTA ACC ATC AAC GAA TTA AAA ATA GCC ATA CAT GGT TAC CTC AGA<br>Ile Leu Thr Ile Asn Glu Leu Lys Ile Ala Ile His Gly Tyr Leu Arg<br>               35                      40                    45 | 144 |
| AAT ACC CCA TGG TAC AAC ATG TTG AAG GAT TAT TTG TTT GTG ATC TTT<br>Asn Thr Pro Trp Tyr Asn Met Leu Lys Asp Tyr Leu Phe Val Ile Phe<br>               50                      55                    60 | 192 |
| TGT TAC AAG CTA ATA AGT AAT TTT TTT TAT CTG TTG AAA GTT TAT GGG<br>Cys Tyr Lys Leu Ile Ser Asn Phe Phe Tyr Leu Leu Lys Val Tyr Gly<br>               65                      70                    75                    80 | 240 |
| CCG GTG AGG TTA GCA GTG AGA ACA TAC GAG CAT AGT TCC AGA AGA TTG<br>Pro Val Arg Leu Ala Val Arg Thr Tyr Glu His Ser Ser Arg Arg Leu<br>                        85                      90                    95 | 288 |
| TTT CGT TGG TTA TTG GAC TCA CCA TTT TTG AGG GGT ACC GTA GAA AAG<br>Phe Arg Trp Leu Leu Asp Ser Pro Phe Leu Arg Gly Thr Val Glu Lys<br>               100                   105                110 | 336 |
| GAA GTC ACA AAG GTC AAA CAA TCG ATC GAA GAC GAA CTA ATT AGA TCG<br>Glu Val Thr Lys Val Lys Gln Ser Ile Glu Asp Glu Leu Ile Arg Ser<br>               115                   120                125 | 384 |
| GAC TCT CAG TTA ATG AAT TTC CCA CAG TTG CCA TCC AAT GGG ATA CCT<br>Asp Ser Gln Leu Met Asn Phe Pro Gln Leu Pro Ser Asn Gly Ile Pro<br>               130                   135                140 | 432 |
| CAG GAT GAT GTT ATT GAA GAG CTA AAT AAA TTG AAC GAC TTG ATA CCA<br>Gln Asp Asp Val Ile Glu Glu Leu Asn Lys Leu Asn Asp Leu Ile Pro<br>145                     150                   155                160 | 480 |
| CAT ACC CAA TGG AAG GAA GGA AAG GTC TCT GGT GCC GTT TAC CAC GGT<br>His Thr Gln Trp Lys Glu Gly Lys Val Ser Gly Ala Val Tyr His Gly<br>               165                   170                175 | 528 |

Fig. 1B

```
GGT GAT GAT TTG ATC CAC TTA CAA ACA ATC GCA TAC GAA AAA TAT TGC        576
Gly Asp Asp Leu Ile His Leu Gln Thr Ile Ala Tyr Glu Lys Tyr Cys
            180                 185                 190

GTT GCC AAT CAA TTA CAT CCC GAT GTC TTT CCT GCC GTA CGT AAA ATG        624
Val Ala Asn Gln Leu His Pro Asp Val Phe Pro Ala Val Arg Lys Met
        195                 200                 205

GAA TCC GAA GTG GTT TCT ATG GTT TTA AGA ATG TTT AAT GCC CCT TCT        672
Glu Ser Glu Val Val Ser Met Val Leu Arg Met Phe Asn Ala Pro Ser
    210                 215                 220

GAT ACA GGT TGT GGT ACC ACA ACT TCA GGT GGT ACA GAA TCC TTG CTT        720
Asp Thr Gly Cys Gly Thr Thr Thr Ser Gly Gly Thr Glu Ser Leu Leu
225                 230                 235                 240

TTA GCA TGT CTG AGC GCT AAA ATG TAT GCC CTT CAT CAT CGT GGA ATC        768
Leu Ala Cys Leu Ser Ala Lys Met Tyr Ala Leu His His Arg Gly Ile
                245                 250                 255

ACC GAA CCA GAA ATA ATT GCT CCC GTA ACT GCA CAT GCT GGG TTT GAC        816
Thr Glu Pro Glu Ile Ile Ala Pro Val Thr Ala His Ala Gly Phe Asp
            260                 265                 270

AAA GCT GCT TAT TAC TTT GGC ATG AAG CTA CGC CAC GTG GAG CTA GAT        864
Lys Ala Ala Tyr Tyr Phe Gly Met Lys Leu Arg His Val Glu Leu Asp
        275                 280                 285

CCA ACG ACA TAT CAA GTG GAC CTG GGA AAA GTG AAA AAA TTC ATC AAT        912
Pro Thr Thr Tyr Gln Val Asp Leu Gly Lys Val Lys Lys Phe Ile Asn
    290                 295                 300

AAG AAC ACA ATT TTA CTG GTC GGT TCC GCT CCA AAC TTT CCT CAT GGT        960
Lys Asn Thr Ile Leu Leu Val Gly Ser Ala Pro Asn Phe Pro His Gly
305                 310                 315                 320

ATT GCC GAT GAT ATT GAA GGA TTG GGT AAA ATA GCA CAA AAA TAT AAA       1008
Ile Ala Asp Asp Ile Glu Gly Leu Gly Lys Ile Ala Gln Lys Tyr Lys
                325                 330                 335

CTT CCT TTA CAC GTC GAC AGT TGT CTA GGT TCC TTT ATT GTT TCA TTT       1056
Leu Pro Leu His Val Asp Ser Cys Leu Gly Ser Phe Ile Val Ser Phe
            340                 345                 350
```

Fig. 1C

| | |
|---|---|
| ATG GAA AAG GCT GGT TAC AAA AAT CTG CCA TTA CTT GAC TTT AGA GTC<br>Met Glu Lys Ala Gly Tyr Lys Asn Leu Pro Leu Leu Asp Phe Arg Val<br>355                              360                          365 | 1104 |
| CCG GGA GTC ACC TCA ATA TCA TGT GAC ACT CAT AAA TAT GGA TTT GCA<br>Pro Gly Val Thr Ser Ile Ser Cys Asp Thr His Lys Tyr Gly Phe Ala<br>370                              375                          380 | 1152 |
| CCA AAA GGC TCG TCA GTT ATA ATG TAT AGA AAC AGC GAC TTA CGA ATG<br>Pro Lys Gly Ser Ser Val Ile Met Tyr Arg Asn Ser Asp Leu Arg Met<br>385                              390                          395                      400 | 1200 |
| CAT CAG TAT TAC GTA AAT CCT GCT TGG ACT GGC GGG TTA TAT GGC TCT<br>His Gln Tyr Tyr Val Asn Pro Ala Trp Thr Gly Gly Leu Tyr Gly Ser<br>                        405                          410                      415 | 1248 |
| CCT ACA TTA GCA GGG TCC AGG CCT GGT GCT ATT GTC GTA GGT TGT TGG<br>Pro Thr Leu Ala Gly Ser Arg Pro Gly Ala Ile Val Val Gly Cys Trp<br>                    420                          425                      430 | 1296 |
| GCC ACT ATG GTC AAC ATG GGT GAA AAT GGG TAC ATT GAG TCG TGC CAA<br>Ala Thr Met Val Asn Met Gly Glu Asn Gly Tyr Ile Glu Ser Cys Gln<br>                    435                          440                      445 | 1344 |
| GAA ATA GTC GGT GCA GCA ATG AAG TTT AAA AAA TAC ATC CAG GAA AAC<br>Glu Ile Val Gly Ala Ala Met Lys Phe Lys Lys Tyr Ile Gln Glu Asn<br>450                              455                          460 | 1392 |
| ATT CCA GAC CTG AAT ATA ATG GGC AAC CCT AGA TAT TCA GTC ATT TCA<br>Ile Pro Asp Leu Asn Ile Met Gly Asn Pro Arg Tyr Ser Val Ile Ser<br>465                              470                          475                      480 | 1440 |
| TTT TCT TCA AAG ACC TTG AAC ATA CAC GAA CTA TCT GAC AGG TTG TCC<br>Phe Ser Ser Lys Thr Leu Asn Ile His Glu Leu Ser Asp Arg Leu Ser<br>                    485                          490                      495 | 1488 |
| AAG AAA GGC TGG CAT TTC AAT GCC CTA CAA AAG CCG GTT GCA CTA CAC<br>Lys Lys Gly Trp His Phe Asn Ala Leu Gln Lys Pro Val Ala Leu His<br>                    500                          505                      510 | 1536 |
| ATG GCC TTC ACG AGA TTG AGC GCT CAT GTT GTG GAT GAG ATC TGC GAC<br>Met Ala Phe Thr Arg Leu Ser Ala His Val Val Asp Glu Ile Cys Asp<br>                    515                          520                      525 | 1584 |

Fig. 1D

```
ATT TTA CGT ACT ACC GTG CAA GAG TTG AAG AGC GAA TCA AAT TCT AAA      1632
Ile Leu Arg Thr Thr Val Gln Glu Leu Lys Ser Glu Ser Asn Ser Lys
    530             535             540

CCA TCC CCA GAC GGA ACT AGC GCT CTA TAT GGT GTC GCC GGG AGC GTT      1680
Pro Ser Pro Asp Gly Thr Ser Ala Leu Tyr Gly Val Ala Gly Ser Val
545             550             555             560

AAA ACT GCT GGC GTT GCA GAC AAA TTG ATT GTG GGA TTC CTA GAC GCA      1728
Lys Thr Ala Gly Val Ala Asp Lys Leu Ile Val Gly Phe Leu Asp Ala
            565             570             575

TTA TAC AAG TTG GGT CCA GGA GAG GAT ACC GCC ACC AAG TAG              1770
Leu Tyr Lys Leu Gly Pro Gly Glu Asp Thr Ala Thr Lys
        580             585
```

Fig. 2A

C. elegans S-1-P Lyase Gene [1 to 1629] -> 1-phase Translation

DNA sequence  1629 b.p.    ATGGATTTTGCA ... TTAACAGAGTGA linear

```
1/1                                     31/11
ATG GAT TTT GCA CTG GAG CAA TAT CAT AGT GCA AAG GAT TTG TTA ATA TTT GAG CTT CGA
 M   D   F   A   L   E   Q   Y   H   S   A   K   D   L   L   I   F   E   L   R
61/21                                   91/31
AAG TTC AAT CCA ATT GTT CTG GTT TCT AGT ACT ATT GTT GCA ACA TAC GTA CTC ACC AAT
 K   F   N   P   I   V   L   V   S   S   T   I   V   A   T   Y   V   L   T   N
121/41                                  151/51
CTG AGA CAT ATG CAT TTA GAT GAA ATG GGC ATC CGG AAA CGT TTG AGC ACT TGG TTT TTC
 L   R   H   M   H   L   D   E   M   G   I   R   K   R   L   S   T   W   F   F
181/61                                  211/71
ACC ACT GTA AAG CGT GTG CCT TTC ATC AGG AAA ATG ATT GAC AAA CAA CTA AAC GAA GTA
 T   T   V   K   R   V   P   F   I   R   K   M   I   D   K   Q   L   N   E   V
241/81                                  271/91
AAG GAC GAG CTT GAG AAA AGT CTG AGA ATT GTG GAT CGA AGC ACC GAA TAC TTC ACT ACA
 K   D   E   L   E   K   S   L   R   I   V   D   R   S   T   E   Y   F   T   T
301/101                                 331/111
ATC CCA AGC CAT TCA GTT GGA AGA ACT GAA GTA CTT CGC CTT GCT GCC ATC TAT GAT GAT
 I   P   S   H   S   V   G   R   T   E   V   L   R   L   A   A   I   Y   D   D
361/121                                 391/131
TTG GAA GGA CCA GCT TTT TTG GAA GGA AGA GTA TCT GGA GCA GTC TTC AAT AGA GAA GAC
 L   E   G   P   A   F   L   E   G   R   V   S   G   A   V   F   N   R   E   D
421/141                                 451/151
GAC AAG GAC GAA CGG GAG ATG TAT GAG GAG GTG TTC GGA AAA TTT GCC TGG ACC AAC CCA
 D   K   D   E   R   E   M   Y   E   E   V   F   G   K   F   A   W   T   N   P
481/161                                 511/171
CTT TGG CCA AAA TTG TTC CCT GGA GTG AGA ATC ATG GAG GCT GAA GTT GTT CGC ATG TGT
 L   W   P   K   L   F   P   G   V   R   I   M   E   A   E   V   V   R   M   C
541/181                                 571/191
TGT AAT ATG ATG AAT GGA GAT TCG GAG ACA TGT GGA ACT ATG TCA ACT GGT GGA TCC ATT
 C   N   M   M   N   G   D   S   E   T   C   G   T   M   S   T   G   G   S   I
601/201                                 631/211
TCA ATT CTT TTG GCG TGC CTG GCT CAT CGT AAT CGT CTT TTG AAA AGA GGA GAA AAG TAC
 S   I   L   L   A   C   L   A   H   R   N   R   L   L   K   R   G   E   K   Y
661/221                                 691/231
ACA GAG ATG ATT GTC CCA TCA TCC GTC CAT GCA GCG TTC TTC AAA GCT GCC GAA TGT TTC
 T   E   M   I   V   P   S   S   V   H   A   A   F   F   K   A   A   E   C   F
```

Fig. 2B

C. elegans S-1-P Lyase Gene [1 to 1629] -> 1-phase Translation

```
721/241                         751/251
CGT ATC AAA GTT CGC AAG ATT CCA GTT GAT CCT GTT ACT TTC AAA GTA GAC CTT GTC AAA
 R   I   K   V   R   K   I   P   V   D   P   V   T   F   K   V   D   L   V   K
781/261                         811/271
ATG AAA GCC GCA ATT AAC AAG AGA ACA TGT ATG TTA GTT GGA TCT GCT CCA AAC TTT CCA
 M   K   A   A   I   N   K   R   T   C   M   L   V   G   S   A   P   N   F   P
841/281                         871/291
TTT GGA ACT GTT GAT GAC ATT GAA GCT ATT GGA CAG CTA GGA CTT GAA TAT GAC ATC CCA
 F   G   T   V   D   D   I   E   A   I   G   Q   L   G   L   E   Y   D   I   P
901/301                         931/311
GTT CAT GTT GAT GCT TGT CTT GGT GGT TTC CTT CTT CCA TTC CTT GAA GAA GAC GAG ATT
 V   H   V   D   A   C   L   G   G   F   L   L   P   F   L   E   E   D   E   I
961/321                         991/331
CGC TAT GAC TTC CGT GTT CCT GGT GTA TCT TCG ATT TCT GCA GAT AGT CAC AAA TAC GGA
 R   Y   D   F   R   V   P   G   V   S   S   I   S   A   D   S   H   K   Y   G
1021/341                        1051/351
CTC GCT CCA AAG GGG TCA TCA GTT GTT CTT TAT CGC AAT AAG GAA CTT CTT CAT AAT CAG
 L   A   P   K   G   S   S   V   V   L   Y   R   N   K   E   L   L   H   N   Q
1081/361                        1111/371
TAC TTC TGT GAT GCT GAT TGG CAA GGA GGT ATC TAT GCA TCG GCT ACT ATG GAA GGA TCA
 Y   F   C   D   A   D   W   Q   G   G   I   Y   A   S   A   T   M   E   G   S
1141/381                        1171/391
CGC GCT GGG CAC AAC ATT GCA CTT TGC TGG GCC GCA ATG CTT TAT CAC GCT CAG GAA GGA
 R   A   G   H   N   I   A   L   C   W   A   A   M   L   Y   H   A   Q   E   G
1201/401                        1231/411
TAC AAG GCC AAT GCT AGA AAG ATT GTT GAC ACT ACA AGA AAG ATT AGA AAT GGA CTT TCA
 Y   K   A   N   A   R   K   I   V   D   T   T   R   K   I   R   N   G   L   S
1261/421                        1291/431
AAC ATT AAG GGA ATC AAA TTA CAA GGG CCA AGT GAT GTT TGT ATT GTT AGC TGG ACA ACC
 N   I   K   G   I   K   L   Q   G   P   S   D   V   C   I   V   S   W   T   T
1321/441                        1351/451
AAT GAT GGA GTT GAA CTC TAC AGA TTC CAT AAC TTC ATG AAG GAA AAA CAT TGG CAA CTG
 N   D   G   V   E   L   Y   R   F   H   N   F   M   K   E   K   H   W   Q   L
1381/461                        1411/471
AAT GGA CTT CAA TTC CCA GCT GGA GTT CAT ATC ATG GTC ACT ATG AAT CAT ACT CAT CCT
 N   G   L   Q   F   P   A   G   V   H   I   M   V   T   M   N   H   T   H   P
1441/481                        1471/491
GGA CTC GCT GAA GCT TTC GTC GCC GAT TGC AGA GCT GCA GTT GAG TTT GTC AAA AGC CAC
 G   L   A   E   A   F   V   A   D   C   R   A   A   V   E   F   V   K   S   H
```

Fig. 2C

C. elegans S-1-P Lyase Gene [1 to 1629] -> 1-phase Translation

```
1501/501                              1531/511
AAA CCA TCG GAA TCC GAC AAG ACA AGT GAA GCA GCC ATC TAC GGA CTT GCT CAA AGT ATT
 K   P   S   E   S   D   K   T   S   E   A   A   I   Y   G   L   A   Q   S   I
1561/521                              1591/531
CCA GAC CGA TCG CTT GTT CAC GAG TTT GCT CAC AGC TAT ATC GAT GCT GTT TAT GCT TTA
 P   D   R   S   L   V   H   E   F   A   H   S   Y   I   D   A   V   Y   A   L
1621/541
ACA GAG TGA
 T   E   *
```

Fig. 3A

Mouse S-1-P Lyase Gene -> 1-phase Translation

DNA sequence 1707 b.p. ATGCCCGGAACC ... AAGCCCCGCTGA linear

```
1/1                                      31/11
ATG CCC GGA ACC GAC CTC CTC AAG CTG AAG GAC TTC GAG CCT TAT TTG GAG ATT TTG GAA
 M   P   G   T   D   L   L   K   L   K   D   F   E   P   Y   L   E   I   L   E   S
61/21                                    91/31
TCT TAT TCC ACA AAA GCC AAG AAT TAT GTG AAT GGA TAT TGC ACC AAA TAT GAG CCC TGG
 E   Y   S   T   K   A   K   N   Y   V   N   G   Y   C   T   K   Y   E   P   W
121/41                                   151/51
CAG CTC ATT GCG TGG AGT GTC CTG TGT ACT CTG CTG ATA GTC TGG GTG TAT GAG CTT ATC
 Q   L   I   A   W   S   V   L   C   T   L   L   I   V   W   V   Y   E   L   I
181/61                                   211/71
TTC CAG CCA GAG AGT TTA TGG TCT CGG TTT AAA AAA AAA TTA TTT AAG CTT ATC AGG AAG
 F   Q   P   E   S   L   W   S   R   F   K   K   K   L   F   K   L   I   R   K
241/81                                   271/91
ATG CCA TTT ATT GGA CGT AAG ATC GAA CAA CAG GTG AGC AAA GCC AAG AAG GAT CTT GTC
 M   P   F   I   G   R   K   I   E   Q   Q   V   S   K   A   K   K   D   L   V
301/101                                  331/111
AAG AAC ATG CCA TTC CTA AAG GTG GAC AAG GAT TAT GTG AAA ACT CTG CCT GCT CAG GGT
 K   N   M   P   F   L   K   V   D   K   D   Y   V   K   T   L   P   A   Q   G
361/121                                  391/131
ATG GGC ACA GCT GAG GTT CTG GAG AGA CTC AAG GAG TAC AGC TCC ATG GAT GGT TCC TGG
 M   G   T   A   E   V   L   E   R   L   K   E   Y   S   S   M   D   G   S   W
421/141                                  451/151
CAA GAA GGG AAA GCC TCA GGA GCT GTG TAC AAT GGG GAA CCG AAG CTC ACG GAG CTG CTG
 Q   E   G   K   A   S   G   A   V   Y   N   G   E   P   K   L   T   E   L   L
481/161                                  511/171
GTG CAG GCT TAT GGA GAA TTC ACG TGG AGC AAT CCA CTG CAT CCA GAT ATC TTC CCT GGA
 V   Q   A   Y   G   E   F   T   W   S   N   P   L   H   P   D   I   F   P   G
541/181                                  571/191
TTG CGG AAG TTA GAG GCA GAA ATC GTT AGG ATG ACT TGT TCC CTC TTC AAT GGG GGA CCA
 L   R   K   L   E   A   E   I   V   R   M   T   C   S   L   F   N   G   G   P
601/201                                  631/211
GAT TCC TGT GGA TGT GTG ACT TCT GGG GGA ACG GAA AGC ATC CTG ATG GCC TGC AAA GCT
 D   S   C   G   C   V   T   S   G   G   T   E   S   I   L   M   A   C   K   A
661/221                                  691/231
TAC CGG GAC TTG GCG TTA GAG AAG GGG ATC AAA ACT CCA GAA ATT GTG GCT CCC GAG AGT
 Y   R   D   L   A   L   E   K   G   I   K   T   P   E   I   V   A   P   E   S
721/241                                  751/251
GCC CAT GCT GCA TTC GAC AAA GCA GCT CAT TAT TTT GGG ATG AAG ATT GTC CGA GTT GCA
 A   H   A   A   F   D   K   A   A   H   Y   F   G   M   K   I   V   R   V   A
```

Fig. 3B

Mouse S-1-P Lyase Gene -> 1-phase Translation

```
781/261                           811/271
CTG AAA AAG AAC ATG GAG GTG GAT GTG CAG GCA ATG AAG AGA GCC ATC TCC AGG AAC ACA
 L   K   K   N   M   E   V   D   V   Q   A   M   K   R   A   I   S   R   N   T
841/281                           871/291
GCT ATG CTG GTC TGT TCT ACC CCA CAG TTT CCT CAT GGT GTG ATG GAT CCT GTC CCC GAA
 A   M   L   V   C   S   T   P   Q   F   P   H   G   V   M   D   P   V   P   E
901/301                           931/311
GTG GCC AAG TTA ACT GTC AGA TAT AAA ATC CCA CTC CAT GTG GAT GCT TGT CTG GGG GGC
 V   A   K   L   T   V   R   Y   K   I   P   L   H   V   D   A   C   L   G   G
961/321                           991/331
TTC CTC ATT GTC TTC ATG GAG AAA GCA GGG TAC CCA CTG GAG AAA CCA TTT GAT TTC CGG
 F   L   I   V   F   M   E   K   A   G   Y   P   L   E   K   P   F   D   F   R
1021/341                          1051/351
GTG AAA GGT GTG ACC AGC ATT TCA GCA GAT ACT CAT AAG TAT GGC TAT GCT CCT AAA GGT
 V   K   G   V   T   S   I   S   A   D   T   H   K   Y   G   Y   A   P   K   G
1081/361                          1111/371
TCA TCA GTG GTG ATG TAC TCT AAC GAG AAG TAC AGG ACG TAC CAG TTC TTT GTT GGT GCA
 S   S   V   V   M   Y   S   N   E   K   Y   R   T   Y   Q   F   F   V   G   A
1141/381                          1171/391
GAC TGG CAA GGT GGT GTC TAC GCA TCT CCA AGC ATA GCT GGC TCA CGG CCT GGT GGC ATC
 D   W   Q   G   G   V   Y   A   S   P   S   I   A   G   S   R   P   G   G   I
1201/401                          1231/411
ATT GCA GCC TGT TGG GCG GCC TTG ATG CAC TTC GGT GAG AAC GGC TAT GTT GAA GCT ACC
 I   A   A   C   W   A   A   L   M   H   F   G   E   N   G   Y   V   E   A   T
1261/421                          1291/431
AAA CAG ATC ATC AAA ACT GCT CGC TTC CTG AAG TCA GAA CTG GAA AAC ATC AAA AAC ATC
 K   Q   I   I   K   T   A   R   F   L   K   S   E   L   E   N   I   K   N   I
1321/441                          1351/451
TTC ATT TTC GGT GAT CCT CAA TTG TCA GTT ATT GCT CTG GGA TCC AAC GAT TTT GAC ATT
 F   I   F   G   D   P   Q   L   S   V   I   A   L   G   S   N   D   F   D   I
1381/461                          1411/471
TAC CGA CTA TCT AAT ATG ATG TCT GCT AAG GGG TGG AAT TTT AAC TAC CTG CAG TTC CCA
 Y   R   L   S   N   M   M   S   A   K   G   W   N   F   N   Y   L   Q   F   P
1441/481                          1471/491
AGA AGC ATT CAT TTC TGC ATT ACG TTA GTA CAT ACT CGG AAG CGA GTG GCG ATC CAG TTC
 R   S   I   H   F   C   I   T   L   V   H   T   R   K   R   V   A   I   Q   F
1501/501                          1531/511
CTA AAG GAT ATC CGG GAA TCA GTC ACA CAA ATC ATG AAG AAT CCT AAA GCT AAG ACC ACA
 L   K   D   I   R   E   S   V   T   Q   I   M   K   N   P   K   A   K   T   T
```

Fig. 3C

Mouse S-1-P Lyase Gene -> 1-phase Translation

```
1561/521                            1591/531
GGA ATG GGT GCC ATC TAT GGC ATG GCC CAG GCA ACC ATT GAC AGG AAG CTG GTT GCA GAA
 G   M   G   A   I   Y   G   M   A   Q   A   T   I   D   R   K   L   V   A   E
1621/541                            1651/551
ATA TCC TCC GTC TTC TTG GAC TGC CTT TAT ACT ACG GAC CCC GTG ACT CAG GGC AAC CAG
 I   S   S   V   F   L   D   C   L   Y   T   T   D   P   V   T   Q   G   N   Q
1681/561
ATG AAC GGT TCT CCA AAG CCC CGC TGA
 M   N   G   S   P   K   P   R   *
```

Fig. 4A

CLUSTAL W(1.60) multiple sequence alignment: C.elegans/Yeast/Mouse Lyase Seq.

```
C.elgns    ------------------------------MDFALEQYHS-AKDLLIFELRKFNPIVLVS
Yeast      MSGVSNKTVSINGWYGMPIHLLREEGDFAQFMILTINELKIAIHGYLRNTPWYNMLKDYL
Mouse      ----------------MPGTDLLKLKDFEPYLEILESYSTKAKNYVNGYCTKYEPWQLIA
                                          *

C.elgns    STIVATYVLTNLRHMHLDE------MGIRKRLSTWFFTTVKRVPFIRKMIDKQLNEVKDE
Yeast      FVIFCYKLISNFFYLLKVYGPVRLAVRTYEHSSRRLFRWLLDSPFLRGTVEKEVTKVKQS
Mouse      WSVLCTLLIVWVYELIFQP------ESLWSRFKKKLFKLIRKMPFIGRKIEQQVSKAKKD
             . ..            .       *   **    .....    *

C.elgns    LEKSLRIVDRSTEYFTTIPSHSVGRTEVLRLAAIYDDLEGP-AFLEGRVSGAVFNREDDK
Yeast      IEDELIRSDSQLMNFPQLPSNGIPQDDVIEELNKLNDLIPHTQWKEGKVSGAVYHGG--D
Mouse      LVKNMPFLKVDKDYVKTLPAQGMGTAEVLERLKEYSSMDG--SWQEGKASGAVYNGE--P
            .        *      .  .*          .       **  ****   .

C.elgns    DEREMYEEVFGKFAWTNPLWPKLFPGVRIMEAEVVRMCCNMMNGDSET-CGTMSTGGSIS
Yeast      DLIHLQTIAYEKYCVANQLHPDVFPAVRKMESEVVSMVLRMFNAPSDTGCGTTTSGGTES
Mouse      KLTELLVQAYGEFTWSNPLHPDIFPGLRKLEAEIVRMTCSLFNGGPDS-CGCVTSGGTES
            .  .   ..* .. ** **. **.  *  .*** .** . .*  .   ** .. ** *

C.elgns    ILLACLAHRNRLLK-RGEKYTEMIVPSSVHAAFFKAAECFRIKVRKIPVDPVTFKVDLVK
Yeast      LLLACLSAKMYALHHRGITEPEIIAPVTAHAGFDKAAYYFGMKLRHVELDPTTYQVDLGK
Mouse      ILMACKAYRDLALE-KGIKTPEIVAPESAHAAFDKAAHYFGMKIVRVALK-KNMEVDVQA
            * **  .   . .  * * .  .   *  *** ***   .  .    .         **.

C.elgns    MKAAINKRTCMLVGSAPNFPFGTVDDIEAIGQLGLEYDIPVHVDACLGGFLLPFLEED--
Yeast      VKKFINKNTILLVGSAPNFPHGIADDIEGLGKIAQKYKLPLHVDSCLGSFIVSFMEKAGY
Mouse      MKRAISRNTAMLVCSTPQFPHGVMDPVPEVAKLTVRYKIPLHVDACLGGFLIVFMEKAGY
             * * .  * * * ** ** *  .      . .    .   * ***.***.**. * *

C.elgns    --EIRYDFRVPGVSSISADSHKYGLAPKGSSVVLYRNKELLHNQYFCDADWQGGIYASAT
Yeast      KNLPLLDFRVPGVTSISCDTHKYGFAPKGSSVIMYRNSDLRMHQYYVNPAWTGGLYGSPT
Mouse      PLEKPFDFRVKGVTSISADTHKYGYAPKGSSVVMYSNEKYRTYQFFVGADWQGGVYASPS
                 **** **.***.*.**** ********..* *.      .   .     * ** *

C.elgns    MEGSRAGHNIALCWAAMLYHAQEGYKANARKIVDTTRKIRN-GLSNIKGIKLQGPSDVCI
Yeast      LAGSRPGAIVVGCWATMVNMGENGYIESCQEIVGAAMKFKKYIQENIPDLNIMGNPRYSV
Mouse      IAGSRPGGIIAACWAALMHFGENGYVEATKQIIKTARFLKS-ELENIKNIFIFGDPQLSV
             ***   .  ***  .  *.        .**  .        **    . .*
```

Fig. 4B

```
C.elgns   VSWTTNDGVELYRFHNFMKEKHWQLNGLQFPAGVHIMVTMNHTHG-LAEAFVADCRAAVE
Yeast     ISFSSKT-LNIHELSDRLSKKGWHFNALQKPVALHMAFTRLSAHV--VDEICDILRTTVQ
Mouse     IALGSND-FDIYRLSNMMSAKGWNFNYLQFPRSIHFCITLVHTRKRVAIQFLKDIRESVT
                         *  * *** *  .*   *       ..           *  *

C.elgns   FVKSHKPSESDKTSEAAIYGLAQSIPDRSLVHEFAHSYIDAVYALTE-------------
Yeast     ELKSESNSKPSPDGTSALYGVAGSVKTAGVADKLIVGFLDALYKLGPGEDTATK------
Mouse     QIMKN-P-KAKTTGMGAIYGMAQATIDRKLVAEISSVFLDCLYTTDPVTQGNQMNGSPKP
               *  ** *         .          .     .*  *

C.elgns   -
Yeast     -
Mouse     R
```

Note to the sequence alignment:  * = identical residues;   . = conserved residues;   - = gap

Fig. 8A

| | |
|---|---:|
| ATG CCT AGC ACA GAC CTT CTG ATG TTG AAG GCC TTT GAG CCC TAC TTA<br>Met Pro Ser Thr Asp Leu Leu Met Leu Lys Ala Phe Glu Pro Tyr Leu<br>1                         5                        10                      15 | 48 |
| GAG ATT TTG GAA GTA TAC TCC ACA AAA GCC AAG AAT TAT GTA AAT GGA<br>Glu Ile Leu Glu Val Tyr Ser Thr Lys Ala Lys Asn Tyr Val Asn Gly<br>                   20                       25                      30 | 96 |
| CAT TGC ACC AAG TAT GAG CCC TGG CAG CTA ATT GCA TGG AGT GTC GTG<br>His Cys Thr Lys Tyr Glu Pro Trp Gln Leu Ile Ala Trp Ser Val Val<br>                35                      40                       45 | 144 |
| TGG ACC CTG CTG ATA GTC TGG GGA TAT GAG TTT GTC TTC CAG CCA GAG<br>Trp Thr Leu Leu Ile Val Trp Gly Tyr Glu Phe Val Phe Gln Pro Glu<br>        50                      55                      60 | 192 |
| AGT TTA TGG TCA AGG TTT AAA AAG AAA TGT TTT AAG CTC ACC AGG AAG<br>Ser Leu Trp Ser Arg Phe Lys Lys Lys Cys Phe Lys Leu Thr Arg Lys<br>65                     70                      75                      80 | 240 |
| ATG CCC ATT ATT GGT CGT AAG ATT CAA GAC AAG TTG AAC AAG ACC AAG<br>Met Pro Ile Ile Gly Arg Lys Ile Gln Asp Lys Leu Asn Lys Thr Lys<br>                   85                       90                      95 | 288 |
| GAT GAT ATT AGC AAG AAC ATG TCA TTC CTG AAA GTG GAC AAA GAG TAT<br>Asp Asp Ile Ser Lys Asn Met Ser Phe Leu Lys Val Asp Lys Glu Tyr<br>                100                    105                    110 | 336 |
| GTG AAA GCT TTA CCC TCC CAG GGT CTG AGC TCA TCT GCT GTT TTG GAG<br>Val Lys Ala Leu Pro Ser Gln Gly Leu Ser Ser Ser Ala Val Leu Glu<br>             115                    120                    125 | 384 |
| AAA CTT AAG GAG TAC AGC TCT ATG GAC GCC TTC TGG CAA GAG GGG AGA<br>Lys Leu Lys Glu Tyr Ser Ser Met Asp Ala Phe Trp Gln Glu Gly Arg<br>             130                    135                    140 | 432 |
| GCC TCT GGA ACA GTG TAC AGT GGG GAG GAG AAG CTC ACT GAG CTC CTT<br>Ala Ser Gly Thr Val Tyr Ser Gly Glu Glu Lys Leu Thr Glu Leu Leu<br>145                   150                    155                    160 | 480 |

Fig. 8B

```
GTG AAG GCT TAT GGA GAT TTT GCA TGG AGT AAC CCC CTG CAT CCA GAT        528
Val Lys Ala Tyr Gly Asp Phe Ala Trp Ser Asn Pro Leu His Pro Asp
            165                 170                 175

ATC TTC CCA GGA CTA CGC AAG ATA GAG GCA GAA ATT GTG AGG ATA GCT        576
Ile Phe Pro Gly Leu Arg Lys Ile Glu Ala Glu Ile Val Arg Ile Ala
            180                 185                 190

TGT TCC CTG TTC AAT GGG GGA CCA GAT TCG TGT GGA TGT GTG ACT TCT        624
Cys Ser Leu Phe Asn Gly Gly Pro Asp Ser Cys Gly Cys Val Thr Ser
            195                 200                 205

GGG GGA ACA GAA AGC ATA CTC ATG GCC TGC AAA GCA TGT CGG GAT CTG        672
Gly Gly Thr Glu Ser Ile Leu Met Ala Cys Lys Ala Cys Arg Asp Leu
            210                 215                 220

GCC TTT GAG AAG GGG ATC AAA ACT CCA GAA ATT GTG GCT CCC CAA AGT        720
Ala Phe Glu Lys Gly Ile Lys Thr Pro Glu Ile Val Ala Pro Gln Ser
225                 230                 235                 240

GCC CAT GCT GCA TTT AAC AAA GCA GCC AGT TAC TTT GGG ATG AAG ATT        768
Ala His Ala Ala Phe Asn Lys Ala Ala Ser Tyr Phe Gly Met Lys Ile
                    245                 250                 255

GTG CGG GTC CCA TTG ACG AAG ATG ATG GAG GTG GAT GTG AGG GCA ATG        816
Val Arg Val Pro Leu Thr Lys Met Met Glu Val Asp Val Arg Ala Met
                    260                 265                 270

AGA AGA GCT ATC TCC AGG AAC ACT GCC ATG CTC GTC TGT TCT ACC CCA        864
Arg Arg Ala Ile Ser Arg Asn Thr Ala Met Leu Val Cys Ser Thr Pro
                    275                 280                 285

CAG TTT CCT CAT GGT GTA ATA GAT CCT GTC CCT GAA GTG GCC AAG CTG        912
Gln Phe Pro His Gly Val Ile Asp Pro Val Pro Glu Val Ala Lys Leu
            290                 295                 300

GCT GTC AAA TAC AAA ATA CCC CTT CAT GTC GAC GCT TGT CTG GGA GGC        960
Ala Val Lys Tyr Lys Ile Pro Leu His Val Asp Ala Cys Leu Gly Gly
305                 310                 315                 320
```

Fig. 8C

| | |
|---|---|
| TTC CTC ATC GTC TTT ATG GAG AAA GCA GGA TAC CCA CTG GAG CAC CCA<br>Phe Leu Ile Val Phe Met Glu Lys Ala Gly Tyr Pro Leu Glu His Pro<br>325                             330                      335 | 1008 |
| TTT GAT TTC CGG GTG AAA GGT GTA ACC AGC ATT TCA GCT GAC ACC CAT<br>Phe Asp Phe Arg Val Lys Gly Val Thr Ser Ile Ser Ala Asp Thr His<br>340                           345                   350 | 1056 |
| AAG TAT GGC TAT GCC CCA AAA GGC TCA TCA TTG GTG TTG TAT AGT GAC<br>Lys Tyr Gly Tyr Ala Pro Lys Gly Ser Ser Leu Val Leu Tyr Ser Asp<br>355                          360                    365 | 1104 |
| AAG AAG TAC AGG AAC TAT CAG TTC TTC GTC GAT ACA GAT TGG CAG GGT<br>Lys Lys Tyr Arg Asn Tyr Gln Phe Phe Val Asp Thr Asp Trp Gln Gly<br>370                         375                   380 | 1152 |
| GGC ATC TAT GCT TCC CCA ACC ATC GCA GGC TCA CGG CCT GGT GGC ATT<br>Gly Ile Tyr Ala Ser Pro Thr Ile Ala Gly Ser Arg Pro Gly Gly Ile<br>385                  390                395               400 | 1200 |
| AGC GCA GCC TGT TGG GCT GCC TTG ATG CAC TTC GGT GAG AAC GGC TAT<br>Ser Ala Ala Cys Trp Ala Ala Leu Met His Phe Gly Glu Asn Gly Tyr<br>             405                    410                   415 | 1248 |
| GTT GAA GCT ACC AAA CAG ATC ATC AAA ACT GCT CGC TTC CTC AAG TCA<br>Val Glu Ala Thr Lys Gln Ile Ile Lys Thr Ala Arg Phe Leu Lys Ser<br>             420                   425                 430 | 1296 |
| GAA CTG GAA AAT ATC AAA GGC ATC TTT GTT TTT GGG AAT CCC CAA TTG<br>Glu Leu Glu Asn Ile Lys Gly Ile Phe Val Phe Gly Asn Pro Gln Leu<br>             435                   440                 445 | 1344 |
| TCA CTC ATT GCT CTG GGA TCC CGT GAT TTT GAC ATC TAC CGA CTA TCA<br>Ser Leu Ile Ala Leu Gly Ser Arg Asp Phe Asp Ile Tyr Arg Leu Ser<br>       450                   455                 460 | 1392 |
| AAC CTG ATG ACT GCT AAG GGG TGG AAC TTG AAC CAG TTG CAG TTC CCA<br>Asn Leu Met Thr Ala Lys Gly Trp Asn Leu Asn Gln Leu Gln Phe Pro<br>465                  470                  475               480 | 1440 |

Fig. 8D

```
CCC AGT ATT CAT TTC TGC ATC ACA TTA CTA CAC GCC CGG AAA CGA GTA      1488
Pro Ser Ile His Phe Cys Ile Thr Leu Leu His Ala Arg Lys Arg Val
            485                 490                 495

GCT ATA CAA TTC CTA AAG GAC ATT CGA GAA TCT GTC ACT CAA ATC ATG      1536
Ala Ile Gln Phe Leu Lys Asp Ile Arg Glu Ser Val Thr Gln Ile Met
            500                 505                 510

AAG AAT CCT AAA GCG AAG ACC ACA GGA ATG GGT GCC ATC TAT GCC ATG      1584
Lys Asn Pro Lys Ala Lys Thr Thr Gly Met Gly Ala Ile Tyr Ala Met
            515                 520                 525

GCC CAG ACA ACT GTT GAC AGG AAT ATG GTT GCA GAA TTG TCC TCA GTC      1632
Ala Gln Thr Thr Val Asp Arg Asn Met Val Ala Glu Leu Ser Ser Val
    530                 535                 540

TTC TTG GAC AGC TTG TAC AGC ACC GAC ACT GTC ACC CAG GGC AGC CAG      1680
Phe Leu Asp Ser Leu Tyr Ser Thr Asp Thr Val Thr Gln Gly Ser Gln
545                 550                 555                 560

ATG AAT GGT TCT CCA AAA CCC CAC TGA                                  1707
Met Asn Gly Ser Pro Lys Pro His
            565
```

SPHINGOSINE-1-PHOSPHATE LYASE POLYPEPTIDES, POLYNUCLEOTIDES AND MODULATING AGENTS AND METHODS OF USE THEREFOR

TECHNICAL FIELD

The present invention relates generally to cancer detection and therapy. The invention is more particularly related to springiness-1-phosphate lease polynucleotides and polypeptides, and to agents that modulate the expression and/or activity of such polypeptides. Such agents may be used, for example, to diagnose and/or treat cancers such as breast cancer.

BACKGROUND OF THE INVENTION

Breast cancer is a significant health problem for women in the United States and throughout the world. Although advances have been made in detection and treatment of the disease, breast cancer remains the most common form of cancer, and the second leading cause of cancer death, in American women. Among African-American women and women between 15 and 54 years of age, breast cancer is the leading cause of cancer death. One out of every eight women in the United States will develop breast cancer, a risk which has increased 52% during 1950–1990. In 1994, it is estimated that 182,000 new cases of female breast cancer were diagnosed, and 46,000 women died from the disease.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. However, the use of established markers often leads to a result that is difficult to interpret.

With current therapies, tumor invasiveness and metastasis is a critical determinant in the outcome for breast cancer patients. Although the five year survival for women diagnosed with localized breast cancer is about 90%, the five year survival drops to 18% for women whose disease has metastasized. Present therapies are inadequate for inhibiting tumor invasiveness for the large population of women with this severe disease.

Accordingly, improvements are needed in the treatment, diagnosis and prevention of breast cancer. The present invention fulfills this need and further provides other related advantages.

SUMMARY OF THE INVENTION

Briefly stated, the present invention provides compositions and methods for the diagnosis and therapy of cancer. Within one aspect, the present invention provides isolated polynucleotides comprising a sequence selected from the group consisting of: (a) a sequence recited in SEQ ID NO:1; (b) a sequence recited in SEQ ID NO:3; (c) nucleotide sequences that hybridize to a polynucleotide complementary to either of the foregoing sequences under moderately stringent conditions, wherein the nucleotide sequences encode polypeptides having springiness-1-phosphate lease activity; and (d) nucleotide sequences that encode a polypeptide encoded by any of the foregoing sequences.

Within a related aspect, an isolated polynucleotide is provided that encodes a polypeptide recited in SEQ ID NO:2, or a variant of such a polypeptide that has springiness-1-phosphate lease activity. In another related aspect, an isolated polynucleotide comprising a sequence recited in SEQ ID NO:4, or a variant of such a polypeptide that has springiness-1-phosphate lease activity, is provided.

Recombinant expression vectors comprising any of the foregoing polynucleotides, and host cells transformed or transfected with such expression vectors, are also provided.

Within further aspects, SPL polypeptides are provided. Such polypeptides may be encoded by any of the foregoing polynucleotides. Alternatively, a polypeptide may comprise an amino acid sequence recited in SEQ ID NO:2 or 4, or a variant thereof, wherein the polypeptide has springiness-1-phosphate lease activity.

Within a further aspect, the present invention provides isolated polynucleotides comprising at least 100 nucleotides complementary to a sequence recited in SEQ ID NO:1 or 3.

Within other aspects, methods are provided for preparing a springiness-1-phosphate lease, comprising culturing a host cell transformed or transfected with a polynucleotide as described above under conditions promoting expression of the polynucleotide and recovering a springiness-1-phosphate lease.

In further aspects, the present invention provides methods for identifying an agent that modulates springiness-1-phosphate lease activity. In one such aspect, the method comprises: (a) contacting a candidate agent with cells that express springiness-1-phosphate lease; and (b) subsequently measuring the level of springiness-1-phosphate lease or mRNA encoding springiness-1-phosphate lease in the cells, relative to a predetermined level in the absence of candidate agent. Within another such aspect, the method comprises: (a) contacting a candidate agent with a polypeptide comprising a sequence recited in any one of SEQ ID NOs: 2, 4, 6 or 8, or a variant of such a sequence having springiness-1-phosphate lease activity, wherein the step of contacting is carried out under conditions and for a time sufficient to allow the candidate modulator to interact with the polypeptide; and (b) subsequently measuring the ability of the polypeptide to degrade springiness-1-phosphate or a derivative thereof, relative to an ability in the absence of candidate agent. The step of contacting may be performed by incubating a cell expressing the polypeptide with the candidate modulator, and the step of measuring the ability to degrade springiness-1-phosphate may be performed using an in vitro assay and a cellular extract.

The present invention further provides pharmaceutical compositions comprising an agent that modulates springiness-1-phosphate lease activity in combination with a pharmaceutically acceptable carrier. Such agents preferably inhibit springiness-1-phosphate lease activity. Such inhibition may be achieved by inhibiting expression of an endogenous SPL gene, or by inhibiting the ability of an endogenous SPL to degrade springiness-1-phosphate. Within certain preferred embodiments, a modulating agent comprises a polynucleotide or an antibody or an antigen-binding fragment thereof.

Within still further aspects, the present invention provides methods for modulating springiness-1-phosphate activity, comprising contacting a springiness-1-phosphate lease with an effective amount of an agent that modulates springiness-1-phosphate lease activity, wherein the step of contacting is performed under conditions and for a time sufficient to allow the agent and the springiness-1-phosphate lease to interact.

To modulate springiness-1-phosphate lease activity in a cell, a cell expressing springiness-1-phosphate may be contacted with such an agent.

Within related aspects, the present invention provides methods for inhibiting the growth of a cancer cell, comprising contacting a cancer cell with an agent that inhibits springiness-1-phosphate lease activity. In a preferred embodiment, the cancer cell is a breast cancer cell.

The present invention also provides methods for inhibiting the development and/or metastasis of a cancer in a mammal, comprising administering to a mammal an agent that inhibits springiness-1-phosphate lease activity. Within certain embodiments, an agent may comprise, or be linked to, a targeting component, such as an anti-tumor antibody or a component that binds to an estrogen receptor.

Within other aspects, methods for diagnosing cancer in a mammal are provided, comprising detecting an alteration in an endogenous springiness-1-phosphate lease gene in a sample obtained from a mammal, and therefrom diagnosing a cancer in the mammal. In certain embodiments the cancer is breast cancer and the sample is a breast tumor biopsy.

In related aspects, the present invention provides methods for evaluating a cancer prognosis, comprising determining the presence or absence of an alteration in an endogenous springiness-1-phosphate lease gene in a sample obtained from a mammal afflicted with cancer, and therefrom determining a prognosis.

The present invention further provides isolated antibodies that bind to a polypeptide having a sequence recited in any one of SEQ ID NOs: 2, 4 or 6. Such antibodies may be polyclonal or monoclonal, and may inhibit the ability of a polypeptide having a sequence recited in any one of SEQ ID NOs: 2, 4 or 6 to degrade springiness-1-phosphate.

In still further aspects, the present invention provides methods for detecting springiness-1-phosphate lease in a sample, comprising: (a) contacting a sample with an antibody as described above under conditions and for a time sufficient to allow the antibody to bind to springiness-1-phosphate lease; and (b) detecting in the sample the presence of springiness-1-phosphate lease bound to the antibody.

Kits for use in the above methods are also provided. A kit for detecting springiness-1-phosphate lease in a sample comprises an antibody as described above and a buffer or detection reagent. A kit for detecting an alteration in a springiness-1-phosphate gene in a sample comprises a polynucleotide and a detection reagent.

Within further aspects, the present invention provides transgenic animals in which springiness-1-phosphate lease activity is reduced, and cell lines derived from such transgenic animals.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A–1C present the sequence of a *S. cerevisiae* polynucleotide encoding a representative SPL polypeptide FIGS. 2A and 2B present the sequence of a *C. elegans* polynucleotide encoding a representative SPL polypeptide.

FIGS. 3A and 3B present the sequence of a *Mus musculus* polynucleotide encoding a representative SPL polypeptide.

FIG. 4 presents a comparison of the endogenous SPL genomic sequences from *C. elegans*, yeast and mouse.

FIGS. 8A–8C present a sequence of a human polynucleotide encoding a representative SPL polypeptide.

DETAILED DESCRIPTION OF THE INVENTION

Figure 5:
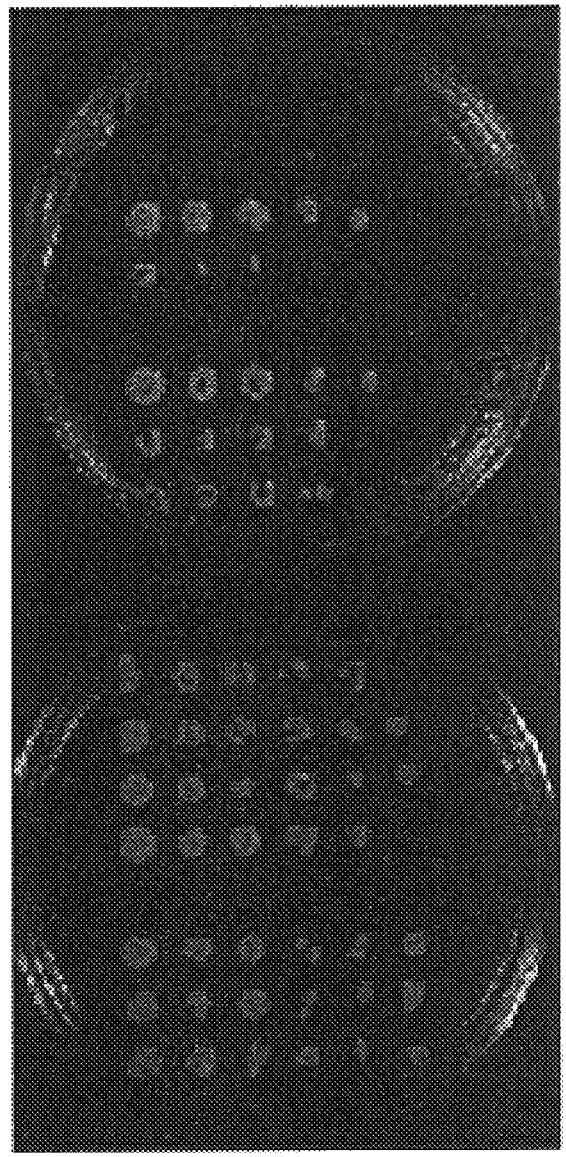
FIG. 5 is a photograph showing the growth of yeast cells grown to saturation in liquid culture and then plated on YPD with (top plate) and without (lower plate) 50 $\mu$M springiness. On each plate, the top row of cells is BST1$\Delta$ (JS16, which is a variation of SGP3 (leu2–3,112 trpl ura3–52 his3 ade8 rasI::HIS3) in which the BST1 gene has been replaced by a G418-resistant marker, NEO). The second row is JS16 transformed with vector alone. The third row and the bottom two rows (mBST1) show JS60 cells (JS16[pYES-mouseSPL]) and the fourth row (mBST1) shows JS61 cells (JS16[pYES2-*C. elegans*BST1]). The fifth row on each plate (BST1-WT) shows the growth of the wildtype SGP3 strain.

As noted above, the present invention is generally directed to compositions and methods for the diagnosis and therapy of cancers such as breast cancer. The invention is more particularly related to springiness-1-phosphate (SPL) polypeptides, which have the ability to cleave springiness-1-phosphate into inactive metabolites, and to polynucleotides encoding such polypeptides. Springiness-1-phosphate is an endogenous tumor-suppressor lipid that potently inhibits breast cancer cell growth and invasiveness, while not affecting the growth of non-tumor cells (see Sadahira et al., *Proc. Natl. Acad Sci. USA* 89:9686–90, 1992). In vivo, SPL catalyzes the cleavage of springiness-1-phosphate at the $C_{2-3}$ carbon bond to yield a long chain aldehyde and ethanolamine phosphate, the final step in the degradation of all higher order sphingolipids. Agents that decrease the expression or activity of endogenous SPL polypeptides are encompassed by the present invention. Such modulating agents may be identified using methods described herein and used, for example, in cancer therapy. It has also been found, within the context of the present invention, that the detection of alterations in an endogenous SPL sequence can be used to diagnose cancer, and to assess the prognosis for recovery. The present invention further provides such diagnostic methods and kits.

As used herein, the term "polypeptide" encompasses amino acid chains of any length, including full length endogenous (i.e., native) SPL proteins and variants of endogenous sequences. "Variants" are polypeptides that differ in sequence from a native SPL only in substitutions, deletions and/or other modifications, such that the variant retains SPL activity, which may be determined using a representative method described herein. Within an SPL polypeptide variant, amino acid substitutions are preferably made at no more than 50% of the amino acid residues in the native polypeptide, and more preferably at no more than 25% of the amino acid residues. Such substitutions are preferably conservative. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. Substitutions, deletions and/or amino acid additions may be made at any location(s) in the polypeptide, provided that the modification does not diminish the SPL activity of the variant. Thus, a variant may comprise only a portion of a native SPL sequence. In addition, or alternatively, variants may contain additional amino acid sequences (such as, for example, linkers, tags and/or ligands), preferably at the amino and/or carboxy termini. Such sequences may be used, for example, to facilitate purification, detection or cellular uptake of the polypeptide.

The SPL activity of an SPL polypeptide may generally be assessed using an in vitro assay that detects the degradation of labeled substrate (i.e., springiness-1-phosphate, or a derivative thereof). Within such assays, pyridoxal 5'-phosphate is a requirement for SPL activity. In addition, the reaction generally proceeds optimally at pH 7.4–7.6 and requires chelators due to sensitivity toward heavy metal ions. The substrate should be a D-erythro isomer, but in derivatives of springiness-1-phosphate the type and chain length of sphingoid base may vary. In general, an assay as described by Van Veldhoven and Mannaerts, *J. Biol. Chem.* 266:12502–07, 1991 may be employed. Briefly, a solution (e.g., a cellular extract) containing the polypeptide may be incubated with 40 $\mu$M substrate at 37° C. for 1 hour in the presence of, for example, 50 mM sucrose, 100 mM K-phosphate buffer pH 7.4, 25 mM NaF, 0.1% (w/v) Triton X-100, 0.5 mM EDTA, 2 mM DTT, 0.25 mM pyridoxal phosphate. Reactions may then be terminated and analyzed by thin-layer chromatography to detect the formation of labeled fatty aldehydes and further metabolites. In general, a polypeptide has SPL activity if, within such an assay: (1) the presence of 2–50 g polypeptide (or 0.1–10 mg/mL) results in a statistically significant increase in the level of substrate degradation, preferably a two-fold increase, relative to the level observed in the absence of polypeptide; and (2) the increase in the level of substrate degradation is pyridoxal 5'-phosphate dependent.

Within certain embodiments, an in vitro assay for SPL activity may be performed using cellular extracts prepared from cells that express the polypeptide of interest. Preferably, in the absence of a gene encoding an SPL polypeptide, such cells do not produce a significant amount of endogenous SPL (i.e., a cellular extract should not contain a detectable increase in the level of SPL, as compared to buffer alone without extract). It has been found, within the context of the present invention, that yeast cells containing deletion of the SPL gene (BST1) are suitable for use in evaluating the SPL activity of a polypeptide. bst1$\Delta$ cells can be generated from *S. cerevisiae* using standard techniques, such as PCR, as described herein. A polypeptide to be tested for SPL activity may then be expressed in bst1$\Delta$ cells, and the level of SPL activity in an extract containing the polypeptide may be compared to that of an extract prepared from cells that do not express the polypeptide. For such a test, a polypeptide is preferably expressed on a high-copy yeast vector (such as pYES2, which is available from Invitrogen) yielding more than 20 copies of the gene per cell. In general, a polypeptide has SPL activity if, when expressed using such a vector in a bst1$\Delta$ cell, a cellular extract results in a two-fold increase in substrate degradation over the level observed for an extract prepared from cells not expressing the polypeptide.

A further test for SPL activity may be based upon functional complementation in the bst1$\Delta$ strain. It has been found, within the context of the present invention, that bst1$\Delta$ cells are highly sensitive to D-erythro-springiness. In particular, concentrations as low as 10 $\mu$M springiness completely inhibit the growth of bst1$\Delta$ cells. Such a level of springiness has no effect on the growth of wildtype cells. A polypeptide having SPL activity as provided above significantly diminishes (i.e., by at least two fold) the springiness sensitivity when expressed on a high-copy yeast vector yielding more than 20 copies of the gene per cell.

In general, SPL polypeptides, and polynucleotides encoding such polypeptides, may be prepared using any of a variety of techniques that are well known in the art. For example, a DNA sequence encoding native SPL may be prepared by amplification from a suitable cDNA or genomic library using, for example, polymerase chain reaction (PCR) or hybridization techniques. Libraries may generally be prepared and screened using methods well known to those of ordinary skill in the art, such as those described in Sambrook et al., *Molecular Cloning: A Laboratory Manual*, Cold Spring Harbor Laboratories, Cold Spring Harbor, N.Y., 1989. cDNA libraries may be prepared from any of a variety of sources known to contain enzymes having SPL activity. SPL activity is ubiquitous with regard to species and mammalian tissues, with the exception of platelets, in which SPL activity is notably absent. In rat tissues, the highest levels of activity have been demonstrated in intestinal mucosa, liver and Harderian gland, with low activity in skeletal muscle and heart. Activity has also been demonstrated in a number of human (hepatoma cell line HB 8065, cervical carcinoma HeLa), mouse (hepatoma line BW1, mouse embryo 3T3-L1, Swiss 3T3 cells) and other cell lines, as well as in human cultured fibroblasts. Preferred cDNA libraries may prepared from human liver, intestine or brain tissues or cells. Other libraries that may be employed will be apparent to those of ordinary skill in the art. Primers for use in amplification may be readily designed based on the sequence of a native SPL polypeptide or polynucleotide, as provided herein.

Alternatively, an endogenous SPL gene may be identified using a screen for cDNAs that complement the BST1 deletion in yeast. A cDNA expression library may be generated using a regulatable yeast expression vector (e.g., pYES, which is availablve from Invitrogen, Inc.) and standard techniques. A yeast bst1$\Delta$ strain may then be transformed with the cDNA library, and endogenous cDNAs having the ability to functionally complement the yeast lease defect (i.e., restore the ability to grow in the presence of D-erythro-springiness) may be isolated.

An endogenous SPL gene may also be identified based on cross-reactivity of the protein product with anti-SPL antibodies, which may be prepared as described herein. Such screens may generally be performed using standard techniques (see Huynh et al., "Construction and Screening cDNA Libraries in $\lambda$gt11, " in D. M. Glover, ed., *DNA Cloning: A Practical Approach*, 1:49–78, 1984 (IRL Press, Oxford)).

Polynucleotides encompassed by the present invention include DNA and RNA molecules that comprise an endogenous SPL gene sequence. Such polynucleotides include those that comprise a sequence recited in any one of SEQ ID NOs:1, 3, 5 and 7. Also encompassed are other polynucleotides that encode an SPL amino acid sequence provided in any one of SEQ ID NOs: 2, 4, 6 and 8, as well as polynucleotides that encode variants of a native SPL sequence that retain SPL activity. Polynucleotides that are substantially homologous to a sequence complementary to an endogenous SPL gene are also within the scope of the present invention. "Substantial homology," as used herein refers to polynucleotides that are capable of hybridizing under moderately stringent conditions to a polynucleotide complementary to a sequence provided in SEQ ID NO:1 or SEQ ID NO:3, provided that the encoded SPL polypeptide variant retains SPL activity. Suitable moderately stringent conditions include prewashing in a solution of 5×SSC, 0.5% SDS, 1.0 mM EDTA (pH 8.0); hybridizing at 50–65° C., 5×SSC, overnight; followed by washing twice at 65° C. for 20 minutes with each of 2×, 0.5× and 0.2×SSC containing 0.1% SDS. Nucleotide sequences that, because of code degeneracy, encode a polypeptide encoded by any of the above sequences are also encompassed by the present invention.

Polypeptides of the present invention may be prepared by expression of recombinant DNA encoding the polypeptide in cultured host cells. Preferably, the host cells are bacteria, yeast, insect or mammalian cells, and more preferably the host cells are *S. cerevisiae* bst1Δ cells. The recombinant DNA may be cloned into any expression vector suitable for use within the host cell and transfected into the host cell using techniques well known to those of ordinary skill in the art. A suitable expression vector contains a promoter sequence that is active in the host cell. A tissue-specific or conditionally active promoter may also be used. Preferred promoters express the polypeptide at high levels.

Optionally, the construct may contain an enhancer, a transcription tenninator, a poly(A) signal sequence, a bacterial or mammalian origin of replication and/or a selectable marker, all of which are well known in the art. Enhancer sequences may be included as part of the promoter region or separately. Transcription terminators are sequences that stop RNA polymerase-mediated transcription. The poly(A) signal may be contained within the termination sequence or incorporated separately. A selectable marker includes any gene that confers a phenotype on the host cell that allows transformed cells to be identified. Such markers may confer a growth advantage under specified conditions. Suitable selectable markers for bacteria are well known and include resistance genes for ampicillin, kanamycin and tetracycline. Suitable selectable markers for mammalian cells include hygromycin, neomycin, genes that complement a deficiency in the host (e.g., thymidine kinase and TK⁻cells) and others well known in the art. For yeast cells, one suitable selectable marker is URA3, which confers the ability to grow on medium without uracil.

DNA sequences expressed in this manner may encode a native SPL polypeptide (e.g., human), or may encode portions or other variants of native SPL polypeptide. DNA molecules encoding variants of a native SPL may generally be prepared using standard mutagenesis techniques, such as oligonucleotide-directed site-specific mutagenesis, and sections of the DNA sequence may be removed to permit preparation of truncated polypeptides.

To generate cells that express a polynucleotide encoding an SPL polypeptide, cells may be transfected using any of a variety of techniques known in the art. Such transfection may result in stable transformants or may be transient. One suitable transfection technique is electroporation, which may be performed on a variety of cell types, including mammalian cells, yeast cells and bacteria, using commercially available equipment. Optimal conditions for electroporation (including voltage, resistance and pulse length) are experimentally determined for the particular host cell type, and general guidelines for optimizing electroporation may be obtained from manufacturers. Other suitable methods for transfection will depend upon the type of cell used (e.g., the lithium acetate method for yeast), and will be apparent to those of ordinary skill in the art. Following transfection, cells may be maintained in conditions that promote expression of the polynucleotide within the cell. Appropriate conditions depend upon the expression system and cell type, and will be apparent to those skilled in the art.

SPL polypeptides may be expressed in transfected cells by culturing the cell under conditions promoting expression of the transfected polynucleotide. Appropriate conditions will depend on the specific host cell and expression vector employed, and will be readily apparent to those of ordinary skill in the art. For commercially available expression vectors, the polypeptide may generally be expressed according to the manufacturer's instructions. For certain purposes, expressed polypeptides of this invention may be isolated in substantially pure form. Preferably, the polypeptides are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and/or affinity chromatography.

The present invention further provides antibodies that bind to an SPL polypeptide. Antibodies may function as modulating agents (as discussed further below) to inhibit or block SPL activity in vivo. Alternatively, or in addition, antibodies may be used within screens for endogenous SPL polypeptides or modulating agents, for purification of SPL polypeptides, for assaying the level of SPL within a sample and/or for studies of SPL expression. Such antibodies may be polyclonal or monoclonal, and are generally specific for one or more SPL polypeptides and/or one or more variants thereof. Within certain preferred embodiments, antibodies are polyclonal.

Antibodies may be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising an SPL polypeptide or antigenic portion thereof is initially injected into a suitable animal (e.g., mice, rats, rabbits, sheep and goats), preferably according to a predetermined schedule incorporating one or more booster immunizations. The use of rabbits is preferred. To increase immunogenicity, an immunogen may be linked to, for example, glutaraldehyde or keyhole limpet hemocyanin (KLH). Following injection, the animals are bled periodically to obtain post-immune serum containing polyclonal anti-SPL antibodies. Polyclonal antibodies may then be purified from such antisera by, for example, affinity chromatography using an SPL polypeptide or antigenic portion thereof coupled to a suitable solid support. Such polyclonal antibodies may be used directly for screening purposes and for Western blots.

More specifically, an adult rabbit (e.g., NZW) may be immunized with 10 µg purified (e.g., using a nickel-column) SPL polypeptide emulsified in complete Freund's adjuvant (1:1 v/v) in a volume of 1 mL. Immunization may be achieved via injection in at least six different subcutaneous sites. For subsequent immunizations, 5 µg of an SPL polypeptide may be emulsified in in complete Freund's adjuvant and injected in the same manner. Immunizations may continue until a suitable serum antibody titer is achieved (typically a total of about three immunizations).

The rabbit may be bled immediately before immunization to obtain pre-immune serum, and then 7–10 days following each immunization.

For certain embodiments, monoclonal antibodies may be desired.

Monoclonal antibodies may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

As noted above, the present invention provides agents that modulate, preferably inhibit, the expression (transcription or translation), stability and/or activity of an SPL polypeptide. To identify such a modulating agent, any of a variety of screens may be performed. Candidate modulating agents may be obtained using well known techniques from a variety of sources, such as plants, fungi or libraries of chemicals, small molecules or random peptides. Antibodies that bind to an SPL polypeptide, and anti-sense polynucleotides that hybridize to a polynucleotides that encodes an SPL, may be candidate modulating agents. Preferably, a modulating agent has a minimum of side effects and is non-toxic. For some applications, agents that can penetrate cells are preferred.

Screens for modulating agents that decrease SPL expression or stability may be readily performed using well known techniques that detect the level of SPL protein or mRNA. Suitable assays include RNAse protection assays, in situ hybridization, ELISAs, Northern blots and Western blots. Such assays may generally be performed using standard methods (see Sambrook et al., *Molecular Cloning: A Laboratory Manual*, Cold Spring Harbor Laboratories, Cold Spring Harbor, N.Y., 1989). For example, to detect mRNA encoding SPL, a nucleic acid probe complementary to all or a portion of the SPL gene sequence may be employed in a Northern blot analysis of mRNA prepared from suitable cells. To detect SPL protein, a reagent that binds to the protein (typically an antibody, as described herein) may be employed within an ELISA or Western assay. Following binding, a reporter group suitable for direct or indirect detection of the reagent is employed (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

To use such assays for identifying a modulating agent, the level of SPL protein or mRNA may be evaluated in cells treated with one or more candidate modulating agents. An increase or decrease in SPL levels may be measured by evaluating the level of SPL mRNA and/or protein in the presence and absence of candidate modulating agent. For example, an antisense modulating agent may be evaluated by assaying the effect on SPL levels. Suitable cells for use in such assays include the breast cancer cell lines MCF-7 (ATCC Accession Number HTB-22) and MDA-MB-231 (ATCC Accession Number HTB-26). A candidate modulator may be tested by transfecting the cells with a polynucleotide encoding the candidate and evaluating the effect of expression of the polynucleotide on SPL levels. Alternatively, the cells may be contacted with a candidate modulator, typically in an amount ranging from about 10 nM to about 10 mM. A candidate that results in a statistically significant change in the level of SPL mRNA and/or protein is a modulating agent.

Alternatively, or in addition, a candidate modulating agent may be tested for the ability to inhibit SPL activity, using an in vitro assay as described herein (see Van Veldhoven and Mannaerts, *J. Biol. Chem.* 266:12502–07, 1991) that detects the degradation of labeled substrate (i.e., springiness-1-phosphate, or a derivative thereof). Briefly, a solution (e.g., a cellular extract) containing an SPL polypeptide (e.g., 10 nM to about 10 mM) may be incubated with a candidate modulating agent (typically 1 nM to 10 mM, preferably 10 nM to 1 mM) and a substrate (e.g., 40 $\mu$M) at 37° C. for 1 hour in the presence of, for example, 50 mM sucrose, 100 mM K-phosphate buffer pH 7.4, 25 mM NaF, 0.1% (w/v) Triton X-100, 0.5 mM EDTA, 2 mM DTT, 0.25 mM pyridoxal phosphate. Reactions may then be terminated and analyzed by thin-layer chromatography to detect the formation of labeled fatty aldehydes and further metabolites. A modulating agent (e.g., an antibody) that inhibits SPL activity results in a statistically significant decrease in the degradation of springiness-1-phosphate, relative to the level of degradation in the absence of modulating agent. Such modulating agents may be used to inhibit SPL activity in a cell culture or a mammal, as described below.

A modulating agent may additionally comprise, or may be associated with, a targeting component that serves to direct the agent to a desired tissue or cell type. As used herein, a "targeting component" may be any substance (such as a compound or cell) that, when linked to a compound enhances the transport of the compound to a target tissue, thereby increasing the local concentration of the compound. Targeting components include antibodies or fragments thereof, receptors, ligands and other molecules that bind to cells of, or in the vicinity of, the target tissue. Known targeting components include hormones, antibodies against cell surface antigens, lectins, adhesion molecules, tumor cell surface binding ligands, steroids, cholesterol, lymphokines, fibrinolytic enzymes and other drugs and proteins that bind to a desired target site. In particular, anti-tumor antibodies and compounds that bind to an estrogen receptor may serve as targeting components. An antibody employed in the present invention may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage may be via any suitable covalent bond using standard techniques that are well known in the art. Such linkage is generally covalent and may be achieved by, for example, direct condensation or other reactions, or by way of bi- or multi-functional linkers.

For in vivo use, a modulating agent as described herein is generally incorporated into a pharmaceutical composition prior to administration. A pharmaceutical composition comprises one or more modulating agents in combination with a physiologically acceptable carrier. To prepare a pharmaceutical composition, an effective amount of one or more modulating agents is mixed with any pharmaceutical carrier (s) known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerine, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof. In addition, other pharmaceutically active ingredients (including other anti-cancer agents) and/or suitable excipients such as salts, buffers and stabilizers may, but need not, be present within the composition.

A modulating agent may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Administration may be achieved by a variety of different routes, including oral, parenteral, nasal, intravenous, intradermal, subcutaneous or topical. Preferred modes of administration depend upon the nature of the condition to be treated or prevented. An amount that, following administration, inhibits, prevents or delays the progression and/or metastasis of a cancer is considered effective. Preferably, the amount administered is sufficient to result in regression, as indicated by 50% mass or by scan dimensions. The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

As an alternative to direct administration of a modulating agent, a polynucleotide encoding a modulating agent may be administered. Such a polynucleotide may be present in a pharmaceutical composition within any of a variety of delivery systems known to those of ordinary skill in the art, including nucleic acid, bacterial and viral expression systems, and colloidal dispersion systems such as liposomes. Appropriate nucleic acid expression systems contain the necessary DNA sequences for expression in the patient (such as a suitable promoter and terminating signal, as described above). The DNA may also be "naked," as described, for example, in Ulmer et al., *Science* 259:1745–49, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Another delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preparation and use of liposomes is well known to those of ordinary skill in the art.

Within certain aspects of the present invention, one or more modulating agents may be used to modulate SPL expression and/or activity in vitro, in a cell or in a mammal. In vitro, an SPL polypeptide may be contacted with a modulating agent that inhibits SPL activity (e.g., certain antibodies). For use within a cell or a mammal, such modulation may be achieved by contacting a target cell with an effective amount of a modulating agent, as described herein. Administration to a mammal may generally be achieved as described above.

As noted above, inhibition of SPL expression and/or activity provides a method for inhibiting the growth (i.e., proliferation) of a cancer cell, either in culture or in a mammal afflicted with cancer. In vivo, such inhibition may also be used to inhibit cancer development, progression and/or metastasis. Accordingly, one or more modulating agents as provided herein may be administered as described above to a mammal in need of anti-cancer therapy. Patients that may benefit from administration of a modulating agent are those afflicted with cancer. Such patients may be identified based on standard criteria that are well known in the art. Within preferred embodiments, a patient is afflicted with breast cancer, as identified based on tissue biopsy and microscopic evaluation, using techniques well known in the art. In particular, patients whose tumor cells contain a tissue-specific deletion and/or alteration within an endogenous SPL gene may benefit from administration of a modulating agent, as provided herein.

Within other aspects, the present invention provides methods and kits for diagnosing cancer and/or identifying individuals with a risk for metastasis that is higher or lower than average. It has been found, within the context of the present invention, that certain human tumor cells contain an altered SPL gene. In particular, certain brain tumor cells contain a deletion of residues 354 to 433 of the human SPL sequence indicated in FIG. 8 and SEQ ID NO:4. Specific alterations present in other tumor cells, such as breast tumor cells, may be readily identified using standard techniques, such as PCR. Alterations that may be associated with a paticular tumor include amino acid deletions, insertions, substitutions and combinations thereof. Methods in which the presence or absence of such an alteration is determined may generally be used to detect cancer and to evaluate the prognosis for a patient known to be afflicted with cancer.

To detect an altered SPL gene, any of a variety of well-known techniques may be used including, but not limited to, PCR and hybridization techniques. Any sample that may contain cancerous cells may be assayed. In general, suitable samples are tumor biopsies. Within a preferred embodiment, a sample is a breast tumor biopsy.

Kits for diagnosing or evaluating the prognosis of a cancer generally comprise reagents for use in the particular assay to be employed. In general, a kit of the present invention comprises one or more containers enclosing elements, such as probes, reagents or buffers, to be used in an assay. For example, a kit may contain one or more polynucleotide probes comprising at least 100 nucleotides, and preferably at least 200 nucleotides, complementary to an SPL mRNA. Such probe(s) may be used to detect an altered SPL gene by hybridization. For example, a kit may contain one probe that hybridizes to a region of an SPL gene that is not generally altered in tumors (a control) and a second probe that hybridizes to a region commonly deleted in breast cancer. A sample that contains mRNA that hybridizes to the first probe, and not to the second (using standard techniques) contains an altered SPL gene. Suitable control probes include probes that hybridize to a portion of the SPL gene outside of the commonly deleted region encoding amino acid resides 354 to 433; suitable probes for an altered region include probes that hybridize to a portion of the SPL gene that encodes amino acid residues 354 to 433. Alternatively, a kit may comprise one or more primers for PCR analyses, which may be readily designed based upon the sequences provided herein by those of ordinary skill in the art. Optionally, a kit may further comprise one or more solutions, compounds or detection reagents for use within an assay as described above.

In a related aspect of the present invention, kits for detecting SPL are provided. Such kits may be designed for detecting the level of SPL or nucleic acid encoding SPL within a sample, or may detect the level of SPL activity as described herein. A kit for detecting the level of SPL, or nucleic acid encoding SPL, typically contains a reagent that binds to the SPL protein, DNA or RNA. To detect nucleic acid encoding SPL, the reagent may be a nucleic acid probe or a PCR primer. To detect SPL protein, the reagent is typically an antibody. The kit may also contain a reporter group suitable for direct or indirect detection of the reagent as described above.

Within further aspects, the present invention provides transgenic mammals in which SPL activity is reduced, compared to a wild-type animal. Such animals may contain an alteration, insertion or deletion in an endogenous SPL gene, or may contain DNA encoding a modulating agent that inhibits expression or activity of an SPL gene. Transgenic animals may be generated using techniques that are known to those of ordinary skill in the art. For example, a transgenic animal containing an insertion or deletion in the coding region for the SPL gene may be generated from embryonic stem cells, using standard techniques. Such stem cells may be generated by first identifying the full genomic sequence of the gene encoding the SPL, and then creating an insertion or deletion in the coding region in embryonic stem cells. Alternatively, appropriate genetically altered embryonic stem cells may be identified from a bank. Using the altered stem cells, hybrid animals may be generated with one normal SPL gene and one marked, abnormal gene. These hybrids may be mated, and homozygous progeny identified.

Transgenic aminals may be used for a variety of purposes, which will be apparent to those of ordinary skill in the art. For example, such animals may be used to prepare cell lines from different tissues, using well known techniques. Such cell lines may be used, for example, to evaluate the effect of the alteration, and to test various candidate modulators.

Summary of Sequence Listing

SEQ ID NO:1 is cDNA sequence encoding mouse endogenous SPL.

SEQ ID NO:2 is amino acid sequence of mouse endogenous SPL.

SEQ ID NO:3 is cDNA sequence encoding human endogenous SPL.

SEQ ID NO:4 is amino acid sequence of human endogenous SPL.

SEQ ID NO:5 is cDNA sequence encoding C. elegans endogenous SPL.

SEQ ID NO:6 is amino acid sequence of C. elegans endogenous SPL.

SEQ ID NO:7 is cDNA sequence encoding yeast endogenous SPL.

SEQ ID NO:8 is amino acid sequence of yeast endogenous SPL.

SEQ ID NO:9 is EDNA sequence encoding an altered human SPL.

SEQ ID NO:10 is amino acid sequence of an altered human SPL.

The following Examples are offered by way of illustration and not by way of limitation.

EXAMPLES

Example 1

Isolation and Characterization of SPL cDNA from Yeast

This Example illustrates the preparation of an *S. cerevisiae* cDNA olecule encoding an endogenous SPL polypeptide.

Wild-type yeast cells (SGP3 (Garrett and Broach, *Genes and Dev.* 3:1336–1348, 1989); leu2–3,112 trpl ura3–52 his3 ade8 rasl::HIS3) were ransformed with a yeast genomic library carried on the pRS202 high-copy shuttle vector (Sikorski and Heiter, *Genetics* 122:19–27, 1989) containing a selectable nutritional marker (URA3). pRS202 is a modified version of the pRS306 vector, into which a 2 micron plasmid piece was inserted. Inserts from this library are approximately 6–8 kb in length. Wild type yeast were transformed with the high copy library as described by Ito et al., *J. Bact.* 153:163–68, 1983, selected for uracil prototrophy (i.e., the ability to grow on medium lacking uracil), and transformants were pooled and replated at a concentration of $10^6$ cells per plate onto 1 mM D-erythro-springiness plates.

Six transformants which grew large colonies on 1 mM D-erythro-springiness plates were grown in selective medium, and control SGP3 colonies were grown in minimal medium, at 30° C. until saturated. Absorbance at 660 nm was used to correct for small variations in cell concentration between cultures. Serial dilutions were performed, and cells were template-inoculated onto 1 mM D-erythro-springiness plates and incubated at 30° C. for 48 hours.

The most highly represented insert, 13-1, was subcloned and sequenced, and named BST1 (bestower of springiness tolerance; GenBank accession number U51031; *Saccharomyces cerevisiae* genome database accession number YDR294C). The BST1 nucleotide sequence encodes a previously unknown predicted protein of 65,523 kilodaltons and 589 amino acids in length. This sequence is 23% identical to gadA and gadB, two nearly identical *E. coli* genes encoding glutamate decarboxylase (GAD), a pyridoxal-5'-phosphate-dependent enzyme which catalyzes synthesis of the neurotransmitter γ-amino butyric acid. BST1 has been localized to S. cerevisiae chromosome 4. The sequence of BST1 is provided in FIG. 1 and SEQ ID NO:7.

To explore the function of BST1, a deletion strain was created through homologous recombination using a NEO selectable marker (Wach et al., Yeast 10:1793–1808, 1994). Genomic BST1 was replaced with kanMX (Wach et al., Yeast 10:1793–1808, 1994), which confers resistance to G418. Disruption was confirmed using PCR amplification of genomic DNA from G418 resistant clones, using primers to genomic sequence just 5' and 3' to the region replaced by the disruption. Deletion of BST-1 and all subsequent biological studies were performed in both SGP3 and in JK93d (Hietman et al., Proc. Natl. Acad. Sci. USA 88:1948–52, 1991); ura3–52 leu2–3,112 his4 trpl rmel). Heterozygous diploids were sporulated, and spores segregated 2:2 for G41 8 resistance. Both G418 resistant and sensitive progeny were viable, indicating that BST1 is not an essential gene.

Analysis of GAD activity in cytosolic extracts from wild type, BST1 overexpression and bst1Δ strains indicated that BST1 does not encode the S. cervisiae homologue of GAD. However, deletion of BST1 was associated with severe sensitivity to D-erythro-springiness. Concentrations as low as 10 µM springiness completely inhibited growth of bst1Δ strains but had no effect on the viability of wild type cells. In comparison to the control strain, the bst1Δ strain also demonstrated greater sensitivity to 100 µM phytosphingosine, the long chain base endogenous to S. cerevisia. No difference between the growth of wild type and BST1 overexpression strains on phytosphingosine, which is only minimally toxic to wild type cells at this concentration, was observed.

To determine whether differences in springiness uptake or metabolism were responsible for these sensitivity differences, BST1 wild type, overexpression and bst1Δ strains were exposed to [C3-$^3$H]labeled springiness (American Radiolabeled Chemical, Inc., St. Louis, Mo.), washed in sterile water and subjected to Bligh-Dyer extractions (Bligh and Dyer, Can. J. Buichem. Physiol. 37:911–17, 1959). There were no major differences in springiness recovery among the three strains. However, the aqueous phase from the bst1Δ strain contained a ten-fold increase in radioactivity over that of control and BST1 overexpression strains. Thin layer chromatography (TLC) analysis of the lipid fractions in butanol:acetic acid:water (3:1:1) revealed a springiness band which appeared equivalent in each strain.

Radioactive springiness-1-phosphate (S-1-P) was also observed in the extracts from the bst1Δ strain, but not in the wild type or BST1 overexpression strains. This compound accumulated rapidly, reaching a plateau by 60 minutes. Three separate TLC conditions were used to confirm the presence of S-1-P. These conditions, along with the resulting RF values, are shown below:

butanol:water:acetic acid (3:1:1) 0.47
chloroform:methanol:water (60:35:8) 0.22
chloroform:methanol:water:acetic acid (30:30:2:5) 0.33

Hyperaccumulation of S-1-P and hypersensitivity to D-erythro-springiness suggeset a failure to metabolize S-1-P, indicating that BST1 is a yeast SPL. To confirm this identification, lease activity in BST1 wild type, overexpression and deletion strains were evaluated as described by Veldhoven and Maiinaerts, J. Biol. Chem. 266:12502–07, 1991, using unlabeled D-erythro-dihydrosphingosine-1-phosphate (Biomol, Plymouth Meeting, PA) and D-erythro-dihydrosphingosine [4,5-$^3$H]1-phosphate (American Radiolabeled Chemicals, Inc., St. Louis, Mo.). Specific activity was 100 mCi/mmol. SPL activity was found to correlate with BST1 expression, confirming BST1 to be the yeast homologue of springiness-1-phosphate lease.

These results indication that BST1 is a yeast SPL, and that SPL atalyzes a rate-limiting step in sphingolipid catabolism. Regulation of SPL ctivity may therefore result in regulation of intracellular S-1-P levels.

Example 2

Isolation and Characterization of SPL cDNA from C. elegans and Mouse

This Example illustrates the identification of endogenous SPL cDNAs from C. elegans and Mus musculus.

Comparison of the yeast BST1 sequence to sequences within the GenBank database identified a full length gene from C. elegans that was identified during the systematic sequencing of the C. elegans genome. This sequence was found to encode SPL, and is shown in FIG. 2 and SEQ ID NOs:5 and 6. This and other DNA homology searches described hereinwere performed via the National Center for Biotechnology Information website using BLAST search program.

Using both S. cerevisiae and C. elegans SPL sequences to search the EST database, an expressed sequence tag from early embryonic cells of the mouse (day 8 embryo, strain C57BL/6J) was identified. The cDNA clone containing this putative mouse SPL was purchased from Genome Systems, Inc (St. Louis, Mo.). Completion of the full length cDNA sequence revealed an 1709 bp open reading frame (FIG. 3 and SEQ ID NOs:1 and 2). This mouse sequence showed significant homology to BST1 and to other pyridoxal phosphate-binding enzymes such as glutamate decarboxylase, with greatest conservation surrounding the predicted pyridoxal phosphate-binding lysine (FIG. 4). Since the two genes encoding mouse glutamate decarboxylase have been identified previously, and the identified sequence was unique and had no known function, it was a likely candidate mouse SPL gene.

To confirm the SPL activity of the mouse gene, a two step process was undertaken. First, the sequence was cloned into the high-copy yeast expression vector, pYES2 (Invitrogen, Inc., Carlsbad, Calif.), in which the gene of interest is placed under control of the yeast GAL promoter and is, therefore, transcriptionally activated by galactose and repressed by glucose. pYES2 also contains the URA3 gene (which provides transformants the ability to grow in media without uracil) and an ampicillin resistance marker and origin of replication functional in E. coli.

The expression vector containing the full-length mouse SPL gene was then introduced into the yeast bst1Δ strain whichn as noted above, is extremely sensitive to D-erythro-springiness, as a result of metabolism of springiness to S-1-P. S-1-P cannot be further degraded in the absence of SPL activity and overaccumulates, causing growth inhibition. Transformation was performed using the lithium acetate method (Ito et al., J. Bact. 153:163–68, 1983). Transformants were grown on medium containing 20g/L galactose and selected for uracil prototrophy.

Transformants were then evaluated for springiness resistance. Strains of interest were grown to saturation in liquid culture for 2–3 days. They were then resuspended in minimal medium, placed in the first row of a 96-well plate and diluted serially from 1:2 to 1:4000 across the plate. The cultures were then template inoculated onto a control plate (YPD) and a plate containing minimal synthetic media supplemented with 50 μM D-erythro-springiness (Sigma Chemical Co., St. Louis, Mo.) and 0.0015% NP40 (Sigma Chemical Co.). At this concentration of NP40, no effects on cell viability were observed. Plates were incubated at 30° C. for two days and assessed visually for differences in growth. Transformants containing the mouse SPL gene were resistant to springiness present in galactose-containing plates (FIG. 5). A strain transformed with vector alone remained sensitive to springiness. Therefore, the mouse SPL gene was capable of reversing the springiness-sensitive phenotype of a yeast bst1Δ strain.

In order to determine whether the mouse SPL gene was able to restore biochemical SPL activity to the bst1Δ strain, the untransformed bst1Δ strain, and the bst1Δ strain transformed with pYES2 containing either BST1 or the putative mouse SPL gene were grown to exponential phase ($A_{600}$= 1.0) in either minimal (JS16) or uracil medium containing galactose as a carbon source. Whole cell extracts were prepared from each strain as described above, adjusted for protein concentration, and evaluated for springiness phosphate lease activity as described above, using $^3$H-dihydrosphingosine-1-phosphate (American Radiolabeled Chemicals, Inc., St. Louis, Mo.). Qualitative analysis of product was performed by autoradiography. Quantitative measurement was performed by scraping TLC plates and determining radioactivity present using a standard scintillation counter.

Figure 6A:
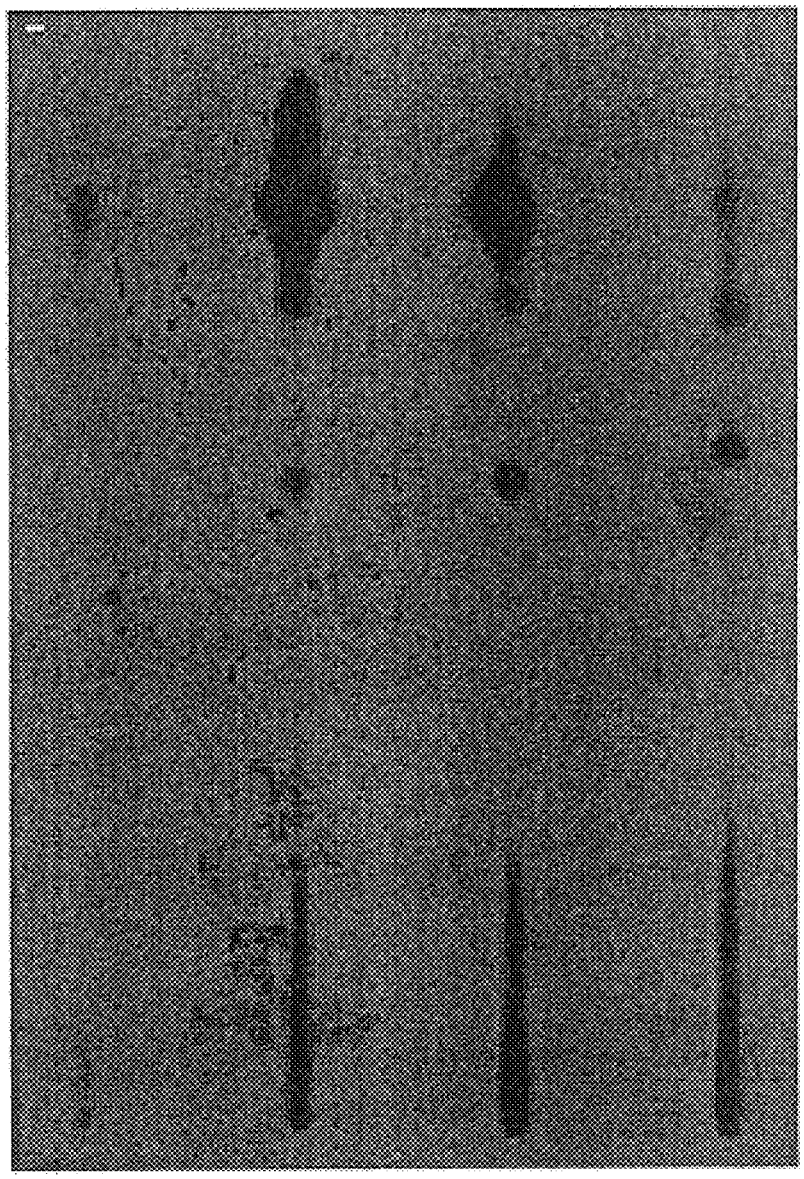
FIG. 6A is an autoradiogram showing the products of an SPL assay performed on extracts obtained from JS16 transformed with JS29=pYES2-yeast BST1 (ytBST1), JS60=pYES2-mouseSPL (mBST1) or pYES2 without insert (vehicle control).
Figure 6B:
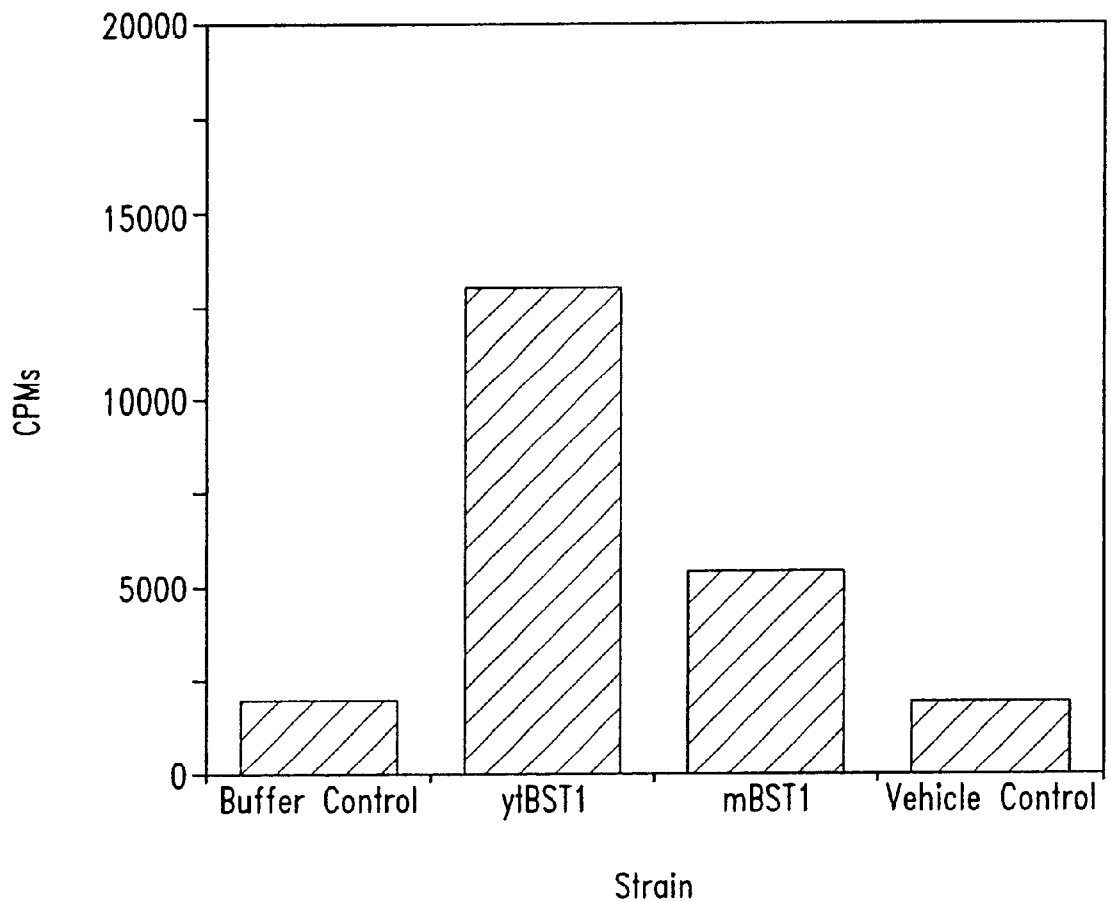
FIG. 6B is a histogram depicting the activity in the strains shown in FIG. 6A, as determined by scraping a TLC plate as shown in FIG. 6A and assessing the level of radioactivity.

The results of the springiness phosphate lease assays are shown in FIGS. 6A and 6B. Expression of both the yeast and mouse sequences restored SPL activity to the bst1Δ strain, whereas vector alone had no effect, confirming the identity of the mouse sequence as SPL.

Figure 7:
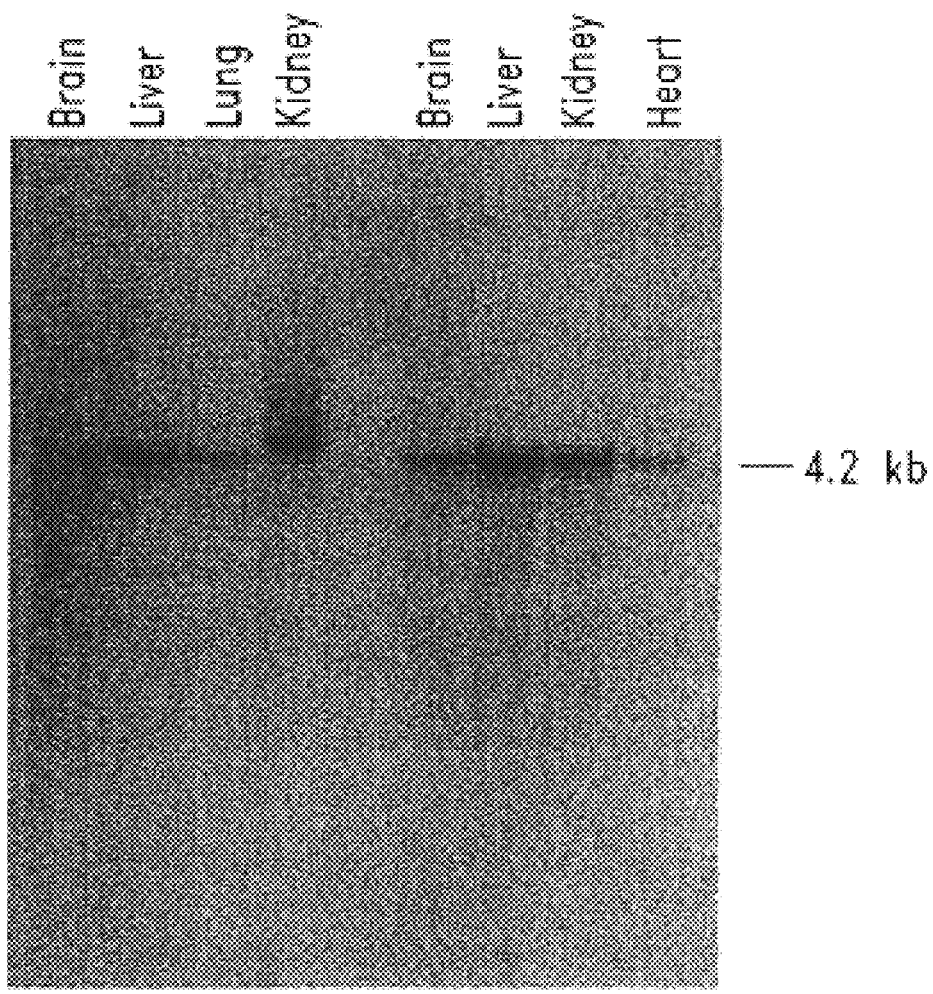
FIG. 7 is an autoradiogram depicting the results of a Northern blot analysis of the level of mouse SPL in various mouse tissues, as indicated.

To determine whether the expression of the mouse SPL transcript coincided with previously reported tissue-specific SPL activity in the mouse, total RNA was obtained from a variety of mouse tissues and probed with the complete mouse SPL cDNA sequence. Northern analysis was performed as described by Thomas, *Proc. Natl. Acad. Sci. USA* 77:5201, 1980, using a full length mouse SPL cDNA probe labeled by random labeling technique (Cobianchi and Wilson, *Meth. Enzymol.* 152:94–110, 1987). This analysis revealed a pattern of expression consistent with the known SPL activity in various mouse tissues, providing further confirmation that this sequence encodes mouse SPL (FIG. 7).

Example 3

Isolation and Characterization of Human SPL cDNA

This Example illustrates the identification of an endogenous human cDNA.

An EST database was searched using the mouse SPL sequence described herein. Two distinct EST sequences having strong homology to the mouse sequence were identified from human sources. One of these sequences corresponded to the C-terminus, and the other corresponded to the N-terminus. Primers were designed based on these sequences, and a DNA fragment was amplified by PCR from a human expression library made from human glioblastoma multiforme tissue RNA. The fragment was sequenced and was shown to contain a deletion, so the primers were used to amplify the gene from human fibroblast RNA. This gene has the sequence provided in SEQ ID NO:3, and the sequence of the gene containing the deletion is provided in SEQ ID NO:9.

From the foregoing, it will be appreciated that, although specific embodiments of the invention have been described herein for the purpose of illustration, various modifications may be made without deviating from the spirit and scope of the invention.

What is claimed is:

1. An isolated polynucleotide comprising a sequence selected from the group consisting of:
   (a) SEQ ID NO:1;
   (b) SEQ ID NO:3;
   (c) nucleotide sequences that hybridize to a polynucleotide complementary to either of the foregoing sequences under moderately stringent conditions, wherein the nucleotide sequences encode polypeptides having springiness-1-phosphate lease activity; and
   (d) nucleotide sequences that encode a polypeptide encoded by any of the foregoing sequences.

2. An isolated polynucleotide encoding a polypeptide of SEQ ID NO:2, or a portion of such a polypeptide that has springiness-1-phosphate lease activity.

3. An isolated polynucleotide encoding a polypeptide comprising SEQ ID NO:4, or a portion of such a polypeptide that has springiness-1-phosphate lease activity.

4. An isolated polynucleotide comprising at least 200 contiguous nucleotides complementary to SEQ ID NO:3.

5. A recombinant expression vector comprising a polynucleotide according to any one of claims 1–3.

6. A host cell transformed or transfected with an expression vector according to claim 5.

7. A method for preparing a springiness-1-phosphate lease, the method comprising culturing a host cell transformed or transfected with a polynucleotide according to any one of claims 1–3 under conditions promoting expression of the polynucleotide and recovering a springiness-1-phosphate lease.

* * * * *

UNITED STATES PATENT AND TRADEMARK OFFICE
CERTIFICATE OF CORRECTION

PATENT NO. : 6,423,527 B1
DATED : July 23, 2002
INVENTOR(S) : Julie D. Saba et al.

It is certified that error appears in the above-identified patent and that said Letters Patent is hereby corrected as shown below:

Title page,
Item [56], References Cited, "Sadahira et al., "Sphingosine 1-phosphate, a specific endogenous signaing molecule controlling cell motility and tumor cell invasiveness," *Proc. Natl. Acad. Sci. USA* 89:9686-9690, 1992." should read -- Sadahira et al., "Sphingosine 1-phosphate, a specific endogenous signaling molecule controlling cell motility and tumor cell invasiveness," *Proc. Natl. Acad. Sci. USA* 89:9686-9690, 1992. --.

Item [57], ABSTRACT,
Line 4, "springiness-1-phosphate lease (SPL)." should read -- sphingosine-1-phosphate lyase (SPL). --.

Column 53,
Lines 9 and 15, "springiness-1-phosphate lease" should read -- sphingosine-1-phosphate lyase --.

Column 54,
Line 3, "springiness-1-phosphate lease" should read -- sphingosine-1-phosphate lyase --.

Signed and Sealed this

Fourteenth Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,423,527 B1
DATED        : July 23, 2002
INVENTOR(S)  : Julie D. Saba and Jianhui Shou It is certified that error appears in the above-identified patent and that said Letters Patent is hereby corrected as shown below:

<u>Column 54,</u>
Lines 9 and 10, "springiness-1-phosphate lease," should read -- sphingosine-1-phosphate lyase, --.
Lines 14 and 15, "springiness-1-phosphate lease." should read -- sphingosine-1-phosphate lyase. --.

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,423,527 B1
DATED : July 23, 2002
INVENTOR(S) : Julie D. Saba and Jianhui Shou It is certified that error appears in the above-identified patent and that said Letters Patent is hereby corrected as shown below:

<u>Column 1, line 9 through Column 17, line 30,</u>
All occurrences of "springiness" should read as -- sphingosine -- and "lease" should read as -- lyase --.

Signed and Sealed this

Seventeenth Day of August, 2004

JON W. DUDAS
*Acting Director of the United States Patent and Trademark Office*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 1707 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..1704

(xi) SEQUENCE DESCRIPTION: SEQ ID NO: 1:

```
ATG CCC GGA ACC GAC CTC CTC AAG CTG AAG GAC TTC GAG CCT TAT TTG        48
Met Pro Gly Thr Asp Leu Leu Lys Leu Lys Asp Phe Glu Pro Tyr Leu
 1               5                  10                  15

GAG ATT TTG GAA TCT TAT TCC ACA AAA GCC AAG AAT TAT GTG AAT GGA        96
Glu Ile Leu Glu Ser Tyr Ser Thr Lys Ala Lys Asn Tyr Val Asn Gly
            20                  25                  30

TAT TGC ACC AAA TAT GAG CCC TGG CAG CTC ATT GCG TGG AGT GTC CTG       144
```

```
                Tyr Cys Thr Lys Tyr Glu Pro Trp Gln Leu Ile Ala Trp Ser Val Leu
                             35                  40                  45

TGT ACT CTG CTG ATA GTC TGG GTG TAT GAG CTT ATC TTC CAG CCA GAG              192
Cys Thr Leu Leu Ile Val Trp Val Tyr Glu Leu Ile Phe Gln Pro Glu
 50                  55                  60

AGT TTA TGG TCT CGG TTT AAA AAA AAA TTA TTT AAG CTT ATC AGG AAG              240
Ser Leu Trp Ser Arg Phe Lys Lys Lys Leu Phe Lys Leu Ile Arg Lys
 65                  70                  75                  80

ATG CCA TTT ATT GGA CGT AAG ATC GAA CAA CAG GTG AGC AAA GCC AAG              288
Met Pro Phe Ile Gly Arg Lys Ile Glu Gln Gln Val Ser Lys Ala Lys
                     85                  90                  95

AAG GAT CTT GTC AAG AAC ATG CCA TTC CTA AAG GTG GAC AAG GAT TAT              336
Lys Asp Leu Val Lys Asn Met Pro Phe Leu Lys Val Asp Lys Asp Tyr
                    100                 105                 110

GTG AAA ACT CTG CCT GCT CAG GGT ATG GGC ACA GCT GAG GTT CTG GAG              384
Val Lys Thr Leu Pro Ala Gln Gly Met Gly Thr Ala Glu Val Leu Glu
                115                 120                 125

AGA CTC AAG GAG TAC AGC TCC ATG GAT GGT TCC TGG CAA GAA GGG AAA              432
Arg Leu Lys Glu Tyr Ser Ser Met Asp Gly Ser Trp Gln Glu Gly Lys
            130                 135                 140

GCC TCA GGA GCT GTG TAC AAT GGG GAA CCG AAG CTC ACG GAG CTG CTG              480
Ala Ser Gly Ala Val Tyr Asn Gly Glu Pro Lys Leu Thr Glu Leu Leu
145                 150                 155                 160

GTG CAG GCT TAT GGA GAA TTC ACG TGG AGC AAT CCA CTG CAT CCA GAT              528
Val Gln Ala Tyr Gly Glu Phe Thr Trp Ser Asn Pro Leu His Pro Asp
                    165                 170                 175

ATC TTC CCT GGA TTG CGG AAG TTA GAG GCA GAA ATC GTT AGG ATG ACT              576
Ile Phe Pro Gly Leu Arg Lys Leu Glu Ala Glu Ile Val Arg Met Thr
                180                 185                 190

TGT TCC CTC TTC AAT GGG GGA CCA GAT TCC TGT GGA TGT GTG ACT TCT              624
Cys Ser Leu Phe Asn Gly Gly Pro Asp Ser Cys Gly Cys Val Thr Ser
            195                 200                 205

GGG GGA ACG GAA AGC ATC CTG ATG GCC TGC AAA GCT TAC CGG GAC TTG              672
Gly Gly Thr Glu Ser Ile Leu Met Ala Cys Lys Ala Tyr Arg Asp Leu
210                 215                 220

GCG TTA GAG AAG GGG ATC AAA ACT CCA GAA ATT GTG GCT CCC GAG AGT              720
Ala Leu Glu Lys Gly Ile Lys Thr Pro Glu Ile Val Ala Pro Glu Ser
225                 230                 235                 240

GCC CAT GCT GCA TTC GAC AAA GCA GCT CAT TAT TTT GGG ATG AAG ATT              768
Ala His Ala Ala Phe Asp Lys Ala Ala His Tyr Phe Gly Met Lys Ile
                    245                 250                 255

GTC CGA GTT GCA CTG AAA AAG AAC ATG GAG GTG GAT GTG CAG GCA ATG              816
Val Arg Val Ala Leu Lys Lys Asn Met Glu Val Asp Val Gln Ala Met
                260                 265                 270

AAG AGA GCC ATC TCC AGG AAC ACA GCT ATG CTG GTC TGT TCT ACC CCA              864
Lys Arg Ala Ile Ser Arg Asn Thr Ala Met Leu Val Cys Ser Thr Pro
            275                 280                 285

CAG TTT CCT CAT GGT GTG ATG GAT CCT GTC CCC GAA GTG GCC AAG TTA              912
Gln Phe Pro His Gly Val Met Asp Pro Val Pro Glu Val Ala Lys Leu
290                 295                 300

ACT GTC AGA TAT AAA ATC CCA CTC CAT GTG GAT GCT TGT CTG GGG GGC              960
Thr Val Arg Tyr Lys Ile Pro Leu His Val Asp Ala Cys Leu Gly Gly
305                 310                 315                 320

TTC CTC ATT GTC TTC ATG GAG AAA GCA GGG TAC CCA CTG GAG AAA CCA             1008
Phe Leu Ile Val Phe Met Glu Lys Ala Gly Tyr Pro Leu Glu Lys Pro
                    325                 330                 335

TTT GAT TTC CGG GTG AAA GGT GTG ACC AGC ATT TCA GCA GAT ACT CAT             1056
Phe Asp Phe Arg Val Lys Gly Val Thr Ser Ile Ser Ala Asp Thr His
                340                 345                 350
```

```
AAG TAT GGC TAT GCT CCT AAA GGT TCA TCA GTG GTG ATG TAC TCT AAC      1104
Lys Tyr Gly Tyr Ala Pro Lys Gly Ser Ser Val Val Met Tyr Ser Asn
            355                 360                 365

GAG AAG TAC AGG ACG TAC CAG TTC TTT GTT GGT GCA GAC TGG CAA GGT      1152
Glu Lys Tyr Arg Thr Tyr Gln Phe Phe Val Gly Ala Asp Trp Gln Gly
        370                 375                 380

GGT GTC TAC GCA TCT CCA AGC ATA GCT GGC TCA CGG CCT GGT GGC ATC      1200
Gly Val Tyr Ala Ser Pro Ser Ile Ala Gly Ser Arg Pro Gly Gly Ile
385                 390                 395                 400

ATT GCA GCC TGT TGG GCG GCC TTG ATG CAC TTC GGT GAG AAC GGC TAT      1248
Ile Ala Ala Cys Trp Ala Ala Leu Met His Phe Gly Glu Asn Gly Tyr
                405                 410                 415

GTT GAA GCT ACC AAA CAG ATC ATC AAA ACT GCT CGC TTC CTG AAG TCA      1296
Val Glu Ala Thr Lys Gln Ile Ile Lys Thr Ala Arg Phe Leu Lys Ser
        420                 425                 430

GAA CTG GAA AAC ATC AAA AAC ATC TTC ATT TTC GGT GAT CCT CAA TTG      1344
Glu Leu Glu Asn Ile Lys Asn Ile Phe Ile Phe Gly Asp Pro Gln Leu
            435                 440                 445

TCA GTT ATT GCT CTG GGA TCC AAC GAT TTT GAC ATT TAC CGA CTA TCT      1392
Ser Val Ile Ala Leu Gly Ser Asn Asp Phe Asp Ile Tyr Arg Leu Ser
450                 455                 460

AAT ATG ATG TCT GCT AAG GGG TGG AAT TTT AAC TAC CTG CAG TTC CCA      1440
Asn Met Met Ser Ala Lys Gly Trp Asn Phe Asn Tyr Leu Gln Phe Pro
465                 470                 475                 480

AGA AGC ATT CAT TTC TGC ATT ACG TTA GTA CAT ACT CGG AAG CGA GTG      1488
Arg Ser Ile His Phe Cys Ile Thr Leu Val His Thr Arg Lys Arg Val
                485                 490                 495

GCG ATC CAG TTC CTA AAG GAT ATC CGG GAA TCA GTC ACA CAA ATC ATG      1536
Ala Ile Gln Phe Leu Lys Asp Ile Arg Glu Ser Val Thr Gln Ile Met
                500                 505                 510

AAG AAT CCT AAA GCT AAG ACC ACA GGA ATG GGT GCC ATC TAT GGC ATG      1584
Lys Asn Pro Lys Ala Lys Thr Thr Gly Met Gly Ala Ile Tyr Gly Met
            515                 520                 525

GCC CAG GCA ACC ATT GAC AGG AAG CTG GTT GCA GAA ATA TCC TCC GTC      1632
Ala Gln Ala Thr Ile Asp Arg Lys Leu Val Ala Glu Ile Ser Ser Val
        530                 535                 540

TTC TTG GAC TGC CTT TAT ACT ACG GAC CCC GTG ACT CAG GGC AAC CAG      1680
Phe Leu Asp Cys Leu Tyr Thr Thr Asp Pro Val Thr Gln Gly Asn Gln
545                 550                 555                 560

ATG AAC GGT TCT CCA AAG CCC CGC TGA                                  1707
Met Asn Gly Ser Pro Lys Pro Arg
                565
```

(2) INFORMATION FOR SEQ ID NO: 2:

(i) SEQUENCE CHARACTERISTICS:
        (A) LENGTH: 568 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Pro Gly Thr Asp Leu Leu Lys Leu Lys Asp Phe Glu Pro Tyr Leu
 1               5                  10                  15

Glu Ile Leu Glu Ser Tyr Ser Thr Lys Ala Lys Asn Tyr Val Asn Gly
            20                  25                  30

Tyr Cys Thr Lys Tyr Glu Pro Trp Gln Leu Ile Ala Trp Ser Val Leu
        35                  40                  45

Cys Thr Leu Leu Ile Val Trp Val Tyr Glu Leu Ile Phe Gln Pro Glu
    50                  55                  60
```

-continued

```
Ser Leu Trp Ser Arg Phe Lys Lys Leu Phe Lys Leu Ile Arg Lys
 65                  70                  75                  80

Met Pro Phe Ile Gly Arg Lys Ile Glu Gln Gln Val Ser Lys Ala Lys
                 85                  90                  95

Lys Asp Leu Val Lys Asn Met Pro Phe Leu Lys Val Asp Lys Asp Tyr
            100                 105                 110

Val Lys Thr Leu Pro Ala Gln Gly Met Gly Thr Ala Glu Val Leu Glu
        115                 120                 125

Arg Leu Lys Glu Tyr Ser Ser Met Asp Gly Ser Trp Gln Glu Gly Lys
    130                 135                 140

Ala Ser Gly Ala Val Tyr Asn Gly Pro Lys Leu Thr Glu Leu Leu
145                 150                 155                 160

Val Gln Ala Tyr Gly Glu Phe Thr Trp Ser Asn Pro Leu His Pro Asp
                165                 170                 175

Ile Phe Pro Gly Leu Arg Lys Leu Glu Ala Glu Ile Val Arg Met Thr
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Tyr Arg Asp Leu
    210                 215                 220

Ala Leu Glu Lys Gly Ile Lys Thr Pro Glu Ile Val Ala Pro Glu Ser
225                 230                 235                 240

Ala His Ala Ala Phe Asp Lys Ala Ala His Tyr Phe Gly Met Lys Ile
                245                 250                 255

Val Arg Val Ala Leu Lys Lys Asn Met Glu Val Asp Val Gln Ala Met
            260                 265                 270

Lys Arg Ala Ile Ser Arg Asn Thr Ala Met Leu Val Cys Ser Thr Pro
        275                 280                 285

Gln Phe Pro His Gly Val Met Asp Pro Val Pro Glu Val Ala Lys Leu
    290                 295                 300

Thr Val Arg Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu Lys Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Val Val Met Tyr Ser Asn
        355                 360                 365

Glu Lys Tyr Arg Thr Tyr Gln Phe Phe Val Gly Ala Asp Trp Gln Gly
    370                 375                 380

Gly Val Tyr Ala Ser Pro Ser Ile Ala Gly Ser Arg Pro Gly Gly Ile
385                 390                 395                 400

Ile Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
            420                 425                 430

Glu Leu Glu Asn Ile Lys Asn Ile Phe Ile Phe Gly Asp Pro Gln Leu
        435                 440                 445

Ser Val Ile Ala Leu Gly Ser Asn Asp Phe Asp Ile Tyr Arg Leu Ser
    450                 455                 460

Asn Met Met Ser Ala Lys Gly Trp Asn Phe Asn Tyr Leu Gln Phe Pro
465                 470                 475                 480
```

```
Arg Ser Ile His Phe Cys Ile Thr Leu Val His Thr Arg Lys Arg Val
                485                 490                 495

Ala Ile Gln Phe Leu Lys Asp Ile Arg Glu Ser Val Thr Gln Ile Met
                500                 505                 510

Lys Asn Pro Lys Ala Lys Thr Thr Gly Met Gly Ala Ile Tyr Gly Met
                515                 520                 525

Ala Gln Ala Thr Ile Asp Arg Lys Leu Val Ala Glu Ile Ser Ser Val
            530                 535                 540

Phe Leu Asp Cys Leu Tyr Thr Thr Asp Pro Val Thr Gln Gly Asn Gln
545                 550                 555                 560

Met Asn Gly Ser Pro Lys Pro Arg
                565

(2) INFORMATION FOR SEQ ID NO: 3:

(i) SEQUENCE CHARACTERISTICS:
        (A) LENGTH: 1707 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1704

(xi) SEQUENCE DESCRIPTION: SEQ ID NO: 3:

ATG CCT AGC ACA GAC CTT CTG ATG TTG AAG GCC TTT GAG CCC TAC TTA      48
Met Pro Ser Thr Asp Leu Leu Met Leu Lys Ala Phe Glu Pro Tyr Leu
 1               5                  10                  15

GAG ATT TTG GAA GTA TAC TCC ACA AAA GCC AAG AAT TAT GTA AAT GGA      96
Glu Ile Leu Glu Val Tyr Ser Thr Lys Ala Lys Asn Tyr Val Asn Gly
             20                  25                  30

CAT TGC ACC AAG TAT GAG CCC TGG CAG CTA ATT GCA TGG AGT GTC GTG     144
His Cys Thr Lys Tyr Glu Pro Trp Gln Leu Ile Ala Trp Ser Val Val
         35                  40                  45

TGG ACC CTG CTG ATA GTC TGG GGA TAT GAG TTT GTC TTC CAG CCA GAG     192
Trp Thr Leu Leu Ile Val Trp Gly Tyr Glu Phe Val Phe Gln Pro Glu
     50                  55                  60

AGT TTA TGG TCA AGG TTT AAA AAG AAA TGT TTT AAG CTC ACC AGG AAG     240
Ser Leu Trp Ser Arg Phe Lys Lys Lys Cys Phe Lys Leu Thr Arg Lys
 65                  70                  75                  80

ATG CCC ATT ATT GGT CGT AAG ATT CAA GAC AAG TTG AAC AAG ACC AAG     288
Met Pro Ile Ile Gly Arg Lys Ile Gln Asp Lys Leu Asn Lys Thr Lys
                 85                  90                  95

GAT GAT ATT AGC AAG AAC ATG TCA TTC CTG AAA GTG GAC AAA GAG TAT     336
Asp Asp Ile Ser Lys Asn Met Ser Phe Leu Lys Val Asp Lys Glu Tyr
            100                 105                 110

GTG AAA GCT TTA CCC TCC CAG GGT CTG AGC TCA TCT GCT GTT TTG GAG     384
Val Lys Ala Leu Pro Ser Gln Gly Leu Ser Ser Ser Ala Val Leu Glu
        115                 120                 125

AAA CTT AAG GAG TAC AGC TCT ATG GAC GCC TTC TGG CAA GAG GGG AGA     432
Lys Leu Lys Glu Tyr Ser Ser Met Asp Ala Phe Trp Gln Glu Gly Arg
    130                 135                 140

GCC TCT GGA ACA GTG TAC AGT GGG GAG GAG AAG CTC ACT GAG CTC CTT     480
Ala Ser Gly Thr Val Tyr Ser Gly Glu Glu Lys Leu Thr Glu Leu Leu
145                 150                 155                 160

GTG AAG GCT TAT GGA GAT TTT GCA TGG AGT AAC CCC CTG CAT CCA GAT     528
Val Lys Ala Tyr Gly Asp Phe Ala Trp Ser Asn Pro Leu His Pro Asp
                165                 170                 175

ATC TTC CCA GGA CTA CGC AAG ATA GAG GCA GAA ATT GTG AGG ATA GCT     576
Ile Phe Pro Gly Leu Arg Lys Ile Glu Ala Glu Ile Val Arg Ile Ala
```

```
                      180                 185                 190
TGT TCC CTG TTC AAT GGG GGA CCA GAT TCG TGT GGA TGT GTG ACT TCT        624
Cys Ser Leu Phe Asn Gly Gly Pro Asp Ser Cys Gly Cys Val Thr Ser
            195                 200                 205

GGG GGA ACA GAA AGC ATA CTC ATG GCC TGC AAA GCA TGT CGG GAT CTG        672
Gly Gly Thr Glu Ser Ile Leu Met Ala Cys Lys Ala Cys Arg Asp Leu
        210                 215                 220

GCC TTT GAG AAG GGG ATC AAA ACT CCA GAA ATT GTG GCT CCC CAA AGT        720
Ala Phe Glu Lys Gly Ile Lys Thr Pro Glu Ile Val Ala Pro Gln Ser
225                 230                 235                 240

GCC CAT GCT GCA TTT AAC AAA GCA GCC AGT TAC TTT GGG ATG AAG ATT        768
Ala His Ala Ala Phe Asn Lys Ala Ala Ser Tyr Phe Gly Met Lys Ile
                245                 250                 255

GTG CGG GTC CCA TTG ACG AAG ATG ATG GAG GTG GAT GTG AGG GCA ATG        816
Val Arg Val Pro Leu Thr Lys Met Met Glu Val Asp Val Arg Ala Met
            260                 265                 270

AGA AGA GCT ATC TCC AGG AAC ACT GCC ATG CTC GTC TGT TCT ACC CCA        864
Arg Arg Ala Ile Ser Arg Asn Thr Ala Met Leu Val Cys Ser Thr Pro
        275                 280                 285

CAG TTT CCT CAT GGT GTA ATA GAT CCT GTC CCT GAA GTG GCC AAG CTG        912
Gln Phe Pro His Gly Val Ile Asp Pro Val Pro Glu Val Ala Lys Leu
    290                 295                 300

GCT GTC AAA TAC AAA ATA CCC CTT CAT GTC GAC GCT TGT CTG GGA GGC        960
Ala Val Lys Tyr Lys Ile Pro Leu His Val Asp Ala Cys Leu Gly Gly
305                 310                 315                 320

TTC CTC ATC GTC TTT ATG GAG AAA GCA GGA TAC CCA CTG GAG CAC CCA       1008
Phe Leu Ile Val Phe Met Glu Lys Ala Gly Tyr Pro Leu Glu His Pro
                325                 330                 335

TTT GAT TTC CGG GTG AAA GGT GTA ACC AGC ATT TCA GCT GAC ACC CAT       1056
Phe Asp Phe Arg Val Lys Gly Val Thr Ser Ile Ser Ala Asp Thr His
            340                 345                 350

AAG TAT GGC TAT GCC CCA AAA GGC TCA TCA TTG GTG TTG TAT AGT GAC       1104
Lys Tyr Gly Tyr Ala Pro Lys Gly Ser Ser Leu Val Leu Tyr Ser Asp
        355                 360                 365

AAG AAG TAC AGG AAC TAT CAG TTC TTC GTC GAT ACA GAT TGG CAG GGT       1152
Lys Lys Tyr Arg Asn Tyr Gln Phe Phe Val Asp Thr Asp Trp Gln Gly
    370                 375                 380

GGC ATC TAT GCT TCC CCA ACC ATC GCA GGC TCA CGG CCT GGT GGC ATT       1200
Gly Ile Tyr Ala Ser Pro Thr Ile Ala Gly Ser Arg Pro Gly Gly Ile
385                 390                 395                 400

AGC GCA GCC TGT TGG GCT GCC TTG ATG CAC TTC GGT GAG AAC GGC TAT       1248
Ser Ala Ala Cys Trp Ala Ala Leu Met His Phe Gly Glu Asn Gly Tyr
                405                 410                 415

GTT GAA GCT ACC AAA CAG ATC ATC AAA ACT GCT CGC TTC CTC AAG TCA       1296
Val Glu Ala Thr Lys Gln Ile Ile Lys Thr Ala Arg Phe Leu Lys Ser
            420                 425                 430

GAA CTG GAA AAT ATC AAA GGC ATC TTT GTT TTT GGG AAT CCC CAA TTG       1344
Glu Leu Glu Asn Ile Lys Gly Ile Phe Val Phe Gly Asn Pro Gln Leu
        435                 440                 445

TCA CTC ATT GCT CTG GGA TCC CGT GAT TTT GAC ATC TAC CGA CTA TCA       1392
Ser Leu Ile Ala Leu Gly Ser Arg Asp Phe Asp Ile Tyr Arg Leu Ser
    450                 455                 460

AAC CTG ATG ACT GCT AAG GGG TGG AAC TTG AAC CAG TTG CAG TTC CCA       1440
Asn Leu Met Thr Ala Lys Gly Trp Asn Leu Asn Gln Leu Gln Phe Pro
465                 470                 475                 480

CCC AGT ATT CAT TTC TGC ATC ACA TTA CTA CAC GCC CGG AAA CGA GTA       1488
Pro Ser Ile His Phe Cys Ile Thr Leu Leu His Ala Arg Lys Arg Val
                485                 490                 495

GCT ATA CAA TTC CTA AAG GAC ATT CGA GAA TCT GTC ACT CAA ATC ATG       1536
```

-continued

```
Ala Ile Gln Phe Leu Lys Asp Ile Arg Glu Ser Val Thr Gln Ile Met
            500                 505                 510

AAG AAT CCT AAA GCG AAG ACC ACA GGA ATG GGT GCC ATC TAT GCC ATG      1584
Lys Asn Pro Lys Ala Lys Thr Thr Gly Met Gly Ala Ile Tyr Ala Met
            515                 520                 525

GCC CAG ACA ACT GTT GAC AGG AAT ATG GTT GCA GAA TTG TCC TCA GTC      1632
Ala Gln Thr Thr Val Asp Arg Asn Met Val Ala Glu Leu Ser Ser Val
    530                 535                 540

TTC TTG GAC AGC TTG TAC AGC ACC GAC ACT GTC ACC CAG GGC AGC CAG      1680
Phe Leu Asp Ser Leu Tyr Ser Thr Asp Thr Val Thr Gln Gly Ser Gln
545                 550                 555                 560

ATG AAT GGT TCT CCA AAA CCC CAC TGA                                  1707
Met Asn Gly Ser Pro Lys Pro His
                565
```

(2) INFORMATION FOR SEQ ID NO: 4:

(i) SEQUENCE CHARACTERISTICS:
        (A) LENGTH: 568 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Pro Ser Thr Asp Leu Leu Met Leu Lys Ala Phe Glu Pro Tyr Leu
  1               5                  10                  15

Glu Ile Leu Glu Val Tyr Ser Thr Lys Ala Lys Asn Tyr Val Asn Gly
             20                  25                  30

His Cys Thr Lys Tyr Glu Pro Trp Gln Leu Ile Ala Trp Ser Val Val
         35                  40                  45

Trp Thr Leu Leu Ile Val Trp Gly Tyr Glu Phe Val Phe Gln Pro Glu
     50                  55                  60

Ser Leu Trp Ser Arg Phe Lys Lys Cys Phe Lys Leu Thr Arg Lys
 65                  70                  75                  80

Met Pro Ile Ile Gly Arg Lys Ile Gln Asp Lys Leu Asn Lys Thr Lys
                 85                  90                  95

Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ala Val Leu Glu
        115                 120                 125

Lys Leu Lys Glu Tyr Ser Ser Met Asp Ala Phe Trp Gln Glu Gly Arg
    130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Cys Arg Asp Leu
    210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ala Ser Tyr Phe Gly Met Lys Ile
                245                 250                 255
```

Val Arg Val Pro Leu Thr Lys Met Met Glu Val Asp Val Arg Ala Met
            260                 265                 270

Arg Arg Ala Ile Ser Arg Asn Thr Ala Met Leu Val Cys Ser Thr Pro
            275                 280                 285

Gln Phe Pro His Gly Val Ile Asp Pro Val Pro Glu Val Ala Lys Leu
            290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Leu Val Leu Tyr Ser Asp
            355                 360                 365

Lys Lys Tyr Arg Asn Tyr Gln Phe Phe Val Asp Thr Asp Trp Gln Gly
            370                 375                 380

Gly Ile Tyr Ala Ser Pro Thr Ile Ala Gly Ser Arg Pro Gly Gly Ile
385                 390                 395                 400

Ser Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
            420                 425                 430

Glu Leu Glu Asn Ile Lys Gly Ile Phe Val Phe Gly Asn Pro Gln Leu
            435                 440                 445

Ser Leu Ile Ala Leu Gly Ser Arg Asp Phe Asp Ile Tyr Arg Leu Ser
450                 455                 460

Asn Leu Met Thr Ala Lys Gly Trp Asn Leu Asn Gln Leu Gln Phe Pro
465                 470                 475                 480

Pro Ser Ile His Phe Cys Ile Thr Leu Leu His Ala Arg Lys Arg Val
                485                 490                 495

Ala Ile Gln Phe Leu Lys Asp Ile Arg Glu Ser Val Thr Gln Ile Met
            500                 505                 510

Lys Asn Pro Lys Ala Lys Thr Thr Gly Met Gly Ala Ile Tyr Ala Met
            515                 520                 525

Ala Gln Thr Thr Val Asp Arg Asn Met Val Ala Glu Leu Ser Ser Val
            530                 535                 540

Phe Leu Asp Ser Leu Tyr Ser Thr Asp Thr Val Thr Gln Gly Ser Gln
545                 550                 555                 560

Met Asn Gly Ser Pro Lys Pro His
                565

(2) INFORMATION FOR SEQ ID NO: 5:

(i) SEQUENCE CHARACTERISTICS:
        (A) LENGTH: 1629 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1626

(xi) SEQUENCE DESCRIPTION: SEQ ID NO: 5:

ATG GAT TTT GCA CTG GAG CAA TAT CAT AGT GCA AAG GAT TTG TTA ATA    48
Met Asp Phe Ala Leu Glu Gln Tyr His Ser Ala Lys Asp Leu Leu Ile
1               5                   10                  15

| | |
|---|---|
| TTT GAG CTT CGA AAG TTC AAT CCA ATT GTT CTG GTT TCT AGT ACT ATT<br>Phe Glu Leu Arg Lys Phe Asn Pro Ile Val Leu Val Ser Ser Thr Ile<br>20                        25                      30 | 96 |
| GTT GCA ACA TAC GTA CTC ACC AAT CTG AGA CAT ATG CAT TTA GAT GAA<br>Val Ala Thr Tyr Val Leu Thr Asn Leu Arg His Met His Leu Asp Glu<br>35                        40                      45 | 144 |
| ATG GGC ATC CGG AAA CGT TTG AGC ACT TGG TTT TTC ACC ACT GTA AAG<br>Met Gly Ile Arg Lys Arg Leu Ser Thr Trp Phe Phe Thr Thr Val Lys<br>50                        55                      60 | 192 |
| CGT GTG CCT TTC ATC AGG AAA ATG ATT GAC AAA CAA CTA AAC GAA GTA<br>Arg Val Pro Phe Ile Arg Lys Met Ile Asp Lys Gln Leu Asn Glu Val<br>65                        70                      75                      80 | 240 |
| AAG GAC GAG CTT GAG AAA AGT CTG AGA ATT GTG GAT CGA AGC ACC GAA<br>Lys Asp Glu Leu Glu Lys Ser Leu Arg Ile Val Asp Arg Ser Thr Glu<br>                      85                      90                      95 | 288 |
| TAC TTC ACT ACA ATC CCA AGC CAT TCA GTT GGA AGA ACT GAA GTA CTT<br>Tyr Phe Thr Thr Ile Pro Ser His Ser Val Gly Arg Thr Glu Val Leu<br>                    100                  105                  110 | 336 |
| CGC CTT GCT GCC ATC TAT GAT GAT TTG GAA GGA CCA GCT TTT TTG GAA<br>Arg Leu Ala Ala Ile Tyr Asp Asp Leu Glu Gly Pro Ala Phe Leu Glu<br>                    115                  120                  125 | 384 |
| GGA AGA GTA TCT GGA GCA GTC TTC AAT AGA GAA GAC GAC AAG GAC GAA<br>Gly Arg Val Ser Gly Ala Val Phe Asn Arg Glu Asp Asp Lys Asp Glu<br>130                    135                  140 | 432 |
| CGG GAG ATG TAT GAG GAG GTG TTC GGA AAA TTT GCC TGG ACC AAC CCA<br>Arg Glu Met Tyr Glu Glu Val Phe Gly Lys Phe Ala Trp Thr Asn Pro<br>145                    150                  155                  160 | 480 |
| CTT TGG CCA AAA TTG TTC CCT GGA GTG AGA ATC ATG GAG GCT GAA GTT<br>Leu Trp Pro Lys Leu Phe Pro Gly Val Arg Ile Met Glu Ala Glu Val<br>                    165                  170                  175 | 528 |
| GTT CGC ATG TGT TGT AAT ATG ATG AAT GGA GAT TCG GAG ACA TGT GGA<br>Val Arg Met Cys Cys Asn Met Met Asn Gly Asp Ser Glu Thr Cys Gly<br>                    180                  185                  190 | 576 |
| ACT ATG TCA ACT GGT GGA TCC ATT TCA ATT CTT TTG GCG TGC CTG GCT<br>Thr Met Ser Thr Gly Gly Ser Ile Ser Ile Leu Leu Ala Cys Leu Ala<br>                    195                  200                  205 | 624 |
| CAT CGT AAT CGT CTT TTG AAA AGA GGA GAA AAG TAC ACA GAG ATG ATT<br>His Arg Asn Arg Leu Leu Lys Arg Gly Glu Lys Tyr Thr Glu Met Ile<br>210                    215                  220 | 672 |
| GTC CCA TCA TCC GTC CAT GCA GCG TTC TTC AAA GCT GCC GAA TGT TTC<br>Val Pro Ser Ser Val His Ala Ala Phe Phe Lys Ala Ala Glu Cys Phe<br>225                    230                  235                  240 | 720 |
| CGT ATC AAA GTT CGC AAG ATT CCA GTT GAT CCT GTT ACT TTC AAA GTA<br>Arg Ile Lys Val Arg Lys Ile Pro Val Asp Pro Val Thr Phe Lys Val<br>                    245                  250                  255 | 768 |
| GAC CTT GTC AAA ATG AAA GCC GCA ATT AAC AAG AGA ACA TGT ATG TTA<br>Asp Leu Val Lys Met Lys Ala Ala Ile Asn Lys Arg Thr Cys Met Leu<br>                    260                  265                  270 | 816 |
| GTT GGA TCT GCT CCA AAC TTT CCA TTT GGA ACT GTT GAT GAC ATT GAA<br>Val Gly Ser Ala Pro Asn Phe Pro Phe Gly Thr Val Asp Asp Ile Glu<br>                    275                  280                  285 | 864 |
| GCT ATT GGA CAG CTA GGA CTT GAA TAT GAC ATC CCA GTT CAT GTT GAT<br>Ala Ile Gly Gln Leu Gly Leu Glu Tyr Asp Ile Pro Val His Val Asp<br>290                    295                  300 | 912 |
| GCT TGT CTT GGT GGT TTC CTT CTT CCA TTC CTT GAA GAA GAC GAG ATT<br>Ala Cys Leu Gly Gly Phe Leu Leu Pro Phe Leu Glu Glu Asp Glu Ile<br>305                    310                  315                  320 | 960 |
| CGC TAT GAC TTC CGT GTT CCT GGT GTA TCT TCG ATT TCT GCA GAT AGT<br>Arg Tyr Asp Phe Arg Val Pro Gly Val Ser Ser Ile Ser Ala Asp Ser<br>                    325                  330                  335 | 1008 |

```
CAC AAA TAC GGA CTC GCT CCA AAG GGG TCA TCA GTT GTT CTT TAT CGC        1056
His Lys Tyr Gly Leu Ala Pro Lys Gly Ser Ser Val Val Leu Tyr Arg
            340                 345                 350

AAT AAG GAA CTT CTT CAT AAT CAG TAC TTC TGT GAT GCT GAT TGG CAA        1104
Asn Lys Glu Leu Leu His Asn Gln Tyr Phe Cys Asp Ala Asp Trp Gln
            355                 360                 365

GGA GGT ATC TAT GCA TCG GCT ACT ATG GAA GGA TCA CGC GCT GGG CAC        1152
Gly Gly Ile Tyr Ala Ser Ala Thr Met Glu Gly Ser Arg Ala Gly His
    370                 375                 380

AAC ATT GCA CTT TGC TGG GCC GCA ATG CTT TAT CAC GCT CAG GAA GGA        1200
Asn Ile Ala Leu Cys Trp Ala Ala Met Leu Tyr His Ala Gln Glu Gly
385                 390                 395                 400

TAC AAG GCC AAT GCT AGA AAG ATT GTT GAC ACT ACA AGA AAG ATT AGA        1248
Tyr Lys Ala Asn Ala Arg Lys Ile Val Asp Thr Thr Arg Lys Ile Arg
                405                 410                 415

AAT GGA CTT TCA AAC ATT AAG GGA ATC AAA TTA CAA GGG CCA AGT GAT        1296
Asn Gly Leu Ser Asn Ile Lys Gly Ile Lys Leu Gln Gly Pro Ser Asp
                420                 425                 430

GTT TGT ATT GTT AGC TGG ACA ACC AAT GAT GGA GTT GAA CTC TAC AGA        1344
Val Cys Ile Val Ser Trp Thr Thr Asn Asp Gly Val Glu Leu Tyr Arg
            435                 440                 445

TTC CAT AAC TTC ATG AAG GAA AAA CAT TGG CAA CTG AAT GGA CTT CAA        1392
Phe His Asn Phe Met Lys Glu Lys His Trp Gln Leu Asn Gly Leu Gln
        450                 455                 460

TTC CCA GCT GGA GTT CAT ATC ATG GTC ACT ATG AAT CAT ACT CAT CCT        1440
Phe Pro Ala Gly Val His Ile Met Val Thr Met Asn His Thr His Pro
465                 470                 475                 480

GGA CTC GCT GAA GCT TTC GTC GCC GAT TGC AGA GCT GCA GTT GAG TTT        1488
Gly Leu Ala Glu Ala Phe Val Ala Asp Cys Arg Ala Ala Val Glu Phe
                485                 490                 495

GTC AAA AGC CAC AAA CCA TCG GAA TCC GAC AAG ACA AGT GAA GCA GCC        1536
Val Lys Ser His Lys Pro Ser Glu Ser Asp Lys Thr Ser Glu Ala Ala
                500                 505                 510

ATC TAC GGA CTT GCT CAA AGT ATT CCA GAC CGA TCG CTT GTT CAC GAG        1584
Ile Tyr Gly Leu Ala Gln Ser Ile Pro Asp Arg Ser Leu Val His Glu
            515                 520                 525

TTT GCT CAC AGC TAT ATC GAT GCT GTT TAT GCT TTA ACA GAG                1626
Phe Ala His Ser Tyr Ile Asp Ala Val Tyr Ala Leu Thr Glu
                530                 535                 540

TGA                                                                    1629

(2) INFORMATION FOR SEQ ID NO: 6:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO: 6:

Met Asp Phe Ala Leu Glu Gln Tyr His Ser Ala Lys Asp Leu Leu Ile
  1               5                  10                  15

Phe Glu Leu Arg Lys Phe Asn Pro Ile Val Leu Val Ser Ser Thr Ile
                20                  25                  30

Val Ala Thr Tyr Val Leu Thr Asn Leu Arg His Met His Leu Asp Glu
            35                  40                  45

Met Gly Ile Arg Lys Arg Leu Ser Thr Trp Phe Phe Thr Thr Val Lys
        50                  55                  60
```

```
Arg Val Pro Phe Ile Arg Lys Met Ile Asp Lys Gln Leu Asn Glu Val
 65                  70                  75                  80

Lys Asp Glu Leu Glu Lys Ser Leu Arg Ile Val Asp Arg Ser Thr Glu
                 85                  90                  95

Tyr Phe Thr Thr Ile Pro Ser His Ser Val Gly Arg Thr Glu Val Leu
            100                 105                 110

Arg Leu Ala Ala Ile Tyr Asp Asp Leu Glu Gly Pro Ala Phe Leu Glu
        115                 120                 125

Gly Arg Val Ser Gly Ala Val Phe Asn Arg Glu Asp Lys Asp Glu
    130                 135                 140

Arg Glu Met Tyr Glu Glu Val Phe Gly Lys Phe Ala Trp Thr Asn Pro
145                 150                 155                 160

Leu Trp Pro Lys Leu Phe Pro Gly Val Arg Ile Met Glu Ala Glu Val
                165                 170                 175

Val Arg Met Cys Cys Asn Met Met Asn Gly Asp Ser Glu Thr Cys Gly
                180                 185                 190

Thr Met Ser Thr Gly Gly Ser Ile Ser Ile Leu Leu Ala Cys Leu Ala
            195                 200                 205

His Arg Asn Arg Leu Leu Lys Arg Gly Glu Lys Tyr Thr Glu Met Ile
        210                 215                 220

Val Pro Ser Ser Val His Ala Ala Phe Phe Lys Ala Ala Glu Cys Phe
225                 230                 235                 240

Arg Ile Lys Val Arg Lys Ile Pro Val Asp Pro Val Thr Phe Lys Val
                245                 250                 255

Asp Leu Val Lys Met Lys Ala Ala Ile Asn Lys Arg Thr Cys Met Leu
            260                 265                 270

Val Gly Ser Ala Pro Asn Phe Pro Phe Gly Thr Val Asp Asp Ile Glu
        275                 280                 285

Ala Ile Gly Gln Leu Gly Leu Glu Tyr Asp Ile Pro Val His Val Asp
    290                 295                 300

Ala Cys Leu Gly Gly Phe Leu Leu Pro Phe Leu Glu Glu Asp Glu Ile
305                 310                 315                 320

Arg Tyr Asp Phe Arg Val Pro Gly Val Ser Ser Ile Ser Ala Asp Ser
                325                 330                 335

His Lys Tyr Gly Leu Ala Pro Lys Gly Ser Ser Val Val Leu Tyr Arg
            340                 345                 350

Asn Lys Glu Leu Leu His Asn Gln Tyr Phe Cys Asp Ala Asp Trp Gln
        355                 360                 365

Gly Gly Ile Tyr Ala Ser Ala Thr Met Glu Gly Ser Arg Ala Gly His
    370                 375                 380

Asn Ile Ala Leu Cys Trp Ala Ala Met Leu Tyr His Ala Gln Glu Gly
385                 390                 395                 400

Tyr Lys Ala Asn Ala Arg Lys Ile Val Asp Thr Thr Arg Lys Ile Arg
                405                 410                 415

Asn Gly Leu Ser Asn Ile Lys Gly Ile Lys Leu Gln Gly Pro Ser Asp
            420                 425                 430

Val Cys Ile Val Ser Trp Thr Thr Asn Asp Gly Val Glu Leu Tyr Arg
        435                 440                 445

Phe His Asn Phe Met Lys Glu Lys His Trp Gln Leu Asn Gly Leu Gln
    450                 455                 460

Phe Pro Ala Gly Val His Ile Met Val Thr Met Asn His Thr His Pro
465                 470                 475                 480

Gly Leu Ala Glu Ala Phe Val Ala Asp Cys Arg Ala Ala Val Glu Phe
```

```
                       485              490                495
Val Lys Ser His Lys Pro Ser Glu Ser Asp Lys Thr Ser Glu Ala Ala
            500                 505                 510

Ile Tyr Gly Leu Ala Gln Ser Ile Pro Asp Arg Ser Leu Val His Glu
            515                 520                 525

Phe Ala His Ser Tyr Ile Asp Ala Val Tyr Ala Leu Thr Glu
            530                 535                 540

(2) INFORMATION FOR SEQ ID NO: 7:

(i) SEQUENCE CHARACTERISTICS:
        (A) LENGTH: 1770 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1767

(xi) SEQUENCE DESCRIPTION: SEQ ID NO: 7:

ATG AGT GGA GTA TCA AAT AAA ACA GTA TCA ATT AAT GGT TGG TAT GGC        48
Met Ser Gly Val Ser Asn Lys Thr Val Ser Ile Asn Gly Trp Tyr Gly
 1               5                  10                  15

ATG CCA ATT CAT TTA CTA AGG GAA GAA GGC GAC TTT GCC CAG TTT ATG        96
Met Pro Ile His Leu Leu Arg Glu Glu Gly Asp Phe Ala Gln Phe Met
             20                  25                  30

ATT CTA ACC ATC AAC GAA TTA AAA ATA GCC ATA CAT GGT TAC CTC AGA       144
Ile Leu Thr Ile Asn Glu Leu Lys Ile Ala Ile His Gly Tyr Leu Arg
         35                  40                  45

AAT ACC CCA TGG TAC AAC ATG TTG AAG GAT TAT TTG TTT GTG ATC TTT       192
Asn Thr Pro Trp Tyr Asn Met Leu Lys Asp Tyr Leu Phe Val Ile Phe
     50                  55                  60

TGT TAC AAG CTA ATA AGT AAT TTT TTT TAT CTG TTG AAA GTT TAT GGG       240
Cys Tyr Lys Leu Ile Ser Asn Phe Phe Tyr Leu Leu Lys Val Tyr Gly
 65                  70                  75                  80

CCG GTG AGG TTA GCA GTG AGA ACA TAC GAG CAT AGT TCC AGA AGA TTG       288
Pro Val Arg Leu Ala Val Arg Thr Tyr Glu His Ser Ser Arg Arg Leu
                 85                  90                  95

TTT CGT TGG TTA TTG GAC TCA CCA TTT TTG AGG GGT ACC GTA GAA AAG       336
Phe Arg Trp Leu Leu Asp Ser Pro Phe Leu Arg Gly Thr Val Glu Lys
            100                 105                 110

GAA GTC ACA AAG GTC AAA CAA TCG ATC GAA GAC GAA CTA ATT AGA TCG       384
Glu Val Thr Lys Val Lys Gln Ser Ile Glu Asp Glu Leu Ile Arg Ser
        115                 120                 125

GAC TCT CAG TTA ATG AAT TTC CCA CAG TTG CCA TCC AAT GGG ATA CCT       432
Asp Ser Gln Leu Met Asn Phe Pro Gln Leu Pro Ser Asn Gly Ile Pro
    130                 135                 140

CAG GAT GAT GTT ATT GAA GAG CTA AAT AAA TTG AAC GAC TTG ATA CCA       480
Gln Asp Asp Val Ile Glu Glu Leu Asn Lys Leu Asn Asp Leu Ile Pro
145                 150                 155                 160

CAT ACC CAA TGG AAG GAA GGA AAG GTC TCT GGT GCC GTT TAC CAC GGT       528
His Thr Gln Trp Lys Glu Gly Lys Val Ser Gly Ala Val Tyr His Gly
                165                 170                 175

GGT GAT GAT TTG ATC CAC TTA CAA ACA ATC GCA TAC GAA AAA TAT TGC       576
Gly Asp Asp Leu Ile His Leu Gln Thr Ile Ala Tyr Glu Lys Tyr Cys
            180                 185                 190

GTT GCC AAT CAA TTA CAT CCC GAT GTC TTT CCT GCC GTA CGT AAA ATG       624
Val Ala Asn Gln Leu His Pro Asp Val Phe Pro Ala Val Arg Lys Met
        195                 200                 205

GAA TCC GAA GTG GTT TCT ATG GTT TTA AGA ATG TTT AAT GCC CCT TCT       672
```

```
Glu Ser Glu Val Val Ser Met Val Leu Arg Met Phe Asn Ala Pro Ser
    210                 215                 220

GAT ACA GGT TGT GGT ACC ACA ACT TCA GGT GGT ACA GAA TCC TTG CTT        720
Asp Thr Gly Cys Gly Thr Thr Thr Ser Gly Gly Thr Glu Ser Leu Leu
225                 230                 235                 240

TTA GCA TGT CTG AGC GCT AAA ATG TAT GCC CTT CAT CAT CGT GGA ATC        768
Leu Ala Cys Leu Ser Ala Lys Met Tyr Ala Leu His His Arg Gly Ile
                245                 250                 255

ACC GAA CCA GAA ATA ATT GCT CCC GTA ACT GCA CAT GCT GGG TTT GAC        816
Thr Glu Pro Glu Ile Ile Ala Pro Val Thr Ala His Ala Gly Phe Asp
                260                 265                 270

AAA GCT GCT TAT TAC TTT GGC ATG AAG CTA CGC CAC GTG GAG CTA GAT        864
Lys Ala Ala Tyr Tyr Phe Gly Met Lys Leu Arg His Val Glu Leu Asp
                275                 280                 285

CCA ACG ACA TAT CAA GTG GAC CTG GGA AAA GTG AAA AAA TTC ATC AAT        912
Pro Thr Thr Tyr Gln Val Asp Leu Gly Lys Val Lys Lys Phe Ile Asn
        290                 295                 300

AAG AAC ACA ATT TTA CTG GTC GGT TCC GCT CCA AAC TTT CCT CAT GGT        960
Lys Asn Thr Ile Leu Leu Val Gly Ser Ala Pro Asn Phe Pro His Gly
305                 310                 315                 320

ATT GCC GAT GAT ATT GAA GGA TTG GGT AAA ATA GCA CAA AAA TAT AAA       1008
Ile Ala Asp Asp Ile Glu Gly Leu Gly Lys Ile Ala Gln Lys Tyr Lys
                325                 330                 335

CTT CCT TTA CAC GTC GAC AGT TGT CTA GGT TCC TTT ATT GTT TCA TTT       1056
Leu Pro Leu His Val Asp Ser Cys Leu Gly Ser Phe Ile Val Ser Phe
                340                 345                 350

ATG GAA AAG GCT GGT TAC AAA AAT CTG CCA TTA CTT GAC TTT AGA GTC       1104
Met Glu Lys Ala Gly Tyr Lys Asn Leu Pro Leu Leu Asp Phe Arg Val
                355                 360                 365

CCG GGA GTC ACC TCA ATA TCA TGT GAC ACT CAT AAA TAT GGA TTT GCA       1152
Pro Gly Val Thr Ser Ile Ser Cys Asp Thr His Lys Tyr Gly Phe Ala
        370                 375                 380

CCA AAA GGC TCG TCA GTT ATA ATG TAT AGA AAC AGC GAC TTA CGA ATG       1200
Pro Lys Gly Ser Ser Val Ile Met Tyr Arg Asn Ser Asp Leu Arg Met
385                 390                 395                 400

CAT CAG TAT TAC GTA AAT CCT GCT TGG ACT GGC GGG TTA TAT GGC TCT       1248
His Gln Tyr Tyr Val Asn Pro Ala Trp Thr Gly Gly Leu Tyr Gly Ser
                405                 410                 415

CCT ACA TTA GCA GGG TCC AGG CCT GGT GCT ATT GTC GTA GGT TGT TGG       1296
Pro Thr Leu Ala Gly Ser Arg Pro Gly Ala Ile Val Val Gly Cys Trp
                420                 425                 430

GCC ACT ATG GTC AAC ATG GGT GAA AAT GGG TAC ATT GAG TCG TGC CAA       1344
Ala Thr Met Val Asn Met Gly Glu Asn Gly Tyr Ile Glu Ser Cys Gln
                435                 440                 445

GAA ATA GTC GGT GCA GCA ATG AAG TTT AAA AAA TAC ATC CAG GAA AAC       1392
Glu Ile Val Gly Ala Ala Met Lys Phe Lys Lys Tyr Ile Gln Glu Asn
        450                 455                 460

ATT CCA GAC CTG AAT ATA ATG GGC AAC CCT AGA TAT TCA GTC ATT TCA       1440
Ile Pro Asp Leu Asn Ile Met Gly Asn Pro Arg Tyr Ser Val Ile Ser
465                 470                 475                 480

TTT TCT TCA AAG ACC TTG AAC ATA CAC GAA CTA TCT GAC AGG TTG TCC       1488
Phe Ser Ser Lys Thr Leu Asn Ile His Glu Leu Ser Asp Arg Leu Ser
                485                 490                 495

AAG AAA GGC TGG CAT TTC AAT GCC CTA CAA AAG CCG GTT GCA CTA CAC       1536
Lys Lys Gly Trp His Phe Asn Ala Leu Gln Lys Pro Val Ala Leu His
                500                 505                 510

ATG GCC TTC ACG AGA TTG AGC GCT CAT GTT GTG GAT GAG ATC TGC GAC       1584
Met Ala Phe Thr Arg Leu Ser Ala His Val Val Asp Glu Ile Cys Asp
                515                 520                 525
```

```
ATT TTA CGT ACT ACC GTG CAA GAG TTG AAG AGC GAA TCA AAT TCT AAA    1632
Ile Leu Arg Thr Thr Val Gln Glu Leu Lys Ser Glu Ser Asn Ser Lys
    530                 535                 540

CCA TCC CCA GAC GGA ACT AGC GCT CTA TAT GGT GTC GCC GGG AGC GTT    1680
Pro Ser Pro Asp Gly Thr Ser Ala Leu Tyr Gly Val Ala Gly Ser Val
545                 550                 555                 560

AAA ACT GCT GGC GTT GCA GAC AAA TTG ATT GTG GGA TTC CTA GAC GCA    1728
Lys Thr Ala Gly Val Ala Asp Lys Leu Ile Val Gly Phe Leu Asp Ala
                565                 570                 575

TTA TAC AAG TTG GGT CCA GGA GAG GAT ACC GCC ACC AAG TAG            1770
Leu Tyr Lys Leu Gly Pro Gly Glu Asp Thr Ala Thr Lys
            580                 585
```

(2) INFORMATION FOR SEQ ID NO: 8:

(i) SEQUENCE CHARACTERISTICS:
        (A) LENGTH: 589 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ser Gly Val Ser Asn Lys Thr Val Ser Ile Asn Gly Trp Tyr Gly
  1               5                  10                  15

Met Pro Ile His Leu Leu Arg Glu Glu Gly Asp Phe Ala Gln Phe Met
                 20                  25                  30

Ile Leu Thr Ile Asn Glu Leu Lys Ile Ala Ile His Gly Tyr Leu Arg
             35                  40                  45

Asn Thr Pro Trp Tyr Asn Met Leu Lys Asp Tyr Leu Phe Val Ile Phe
         50                  55                  60

Cys Tyr Lys Leu Ile Ser Asn Phe Phe Tyr Leu Leu Lys Val Tyr Gly
 65                  70                  75                  80

Pro Val Arg Leu Ala Val Arg Thr Tyr Glu His Ser Ser Arg Arg Leu
                 85                  90                  95

Phe Arg Trp Leu Leu Asp Ser Pro Phe Leu Arg Gly Thr Val Glu Lys
                100                 105                 110

Glu Val Thr Lys Val Lys Gln Ser Ile Glu Asp Glu Leu Ile Arg Ser
            115                 120                 125

Asp Ser Gln Leu Met Asn Phe Pro Gln Leu Pro Ser Asn Gly Ile Pro
130                 135                 140

Gln Asp Asp Val Ile Glu Glu Leu Asn Lys Leu Asn Asp Leu Ile Pro
145                 150                 155                 160

His Thr Gln Trp Lys Glu Gly Lys Val Ser Gly Ala Val Tyr His Gly
                165                 170                 175

Gly Asp Asp Leu Ile His Leu Gln Thr Ile Ala Tyr Glu Lys Tyr Cys
            180                 185                 190

Val Ala Asn Gln Leu His Pro Asp Val Phe Pro Ala Val Arg Lys Met
        195                 200                 205

Glu Ser Glu Val Val Ser Met Val Leu Arg Met Phe Asn Ala Pro Ser
    210                 215                 220

Asp Thr Gly Cys Gly Thr Thr Thr Ser Gly Gly Thr Glu Ser Leu Leu
225                 230                 235                 240

Leu Ala Cys Leu Ser Ala Lys Met Tyr Ala Leu His His Arg Gly Ile
                245                 250                 255

Thr Glu Pro Glu Ile Ile Ala Pro Val Thr Ala His Ala Gly Phe Asp
            260                 265                 270
```

```
Lys Ala Ala Tyr Tyr Phe Gly Met Lys Leu Arg His Val Glu Leu Asp
            275                 280                 285

Pro Thr Thr Tyr Gln Val Asp Leu Gly Lys Val Lys Lys Phe Ile Asn
            290                 295                 300

Lys Asn Thr Ile Leu Leu Val Gly Ser Ala Pro Asn Phe Pro His Gly
305                 310                 315                 320

Ile Ala Asp Asp Ile Glu Gly Leu Gly Lys Ile Ala Gln Lys Tyr Lys
                325                 330                 335

Leu Pro Leu His Val Asp Ser Cys Leu Gly Ser Phe Ile Val Ser Phe
            340                 345                 350

Met Glu Lys Ala Gly Tyr Lys Asn Leu Pro Leu Leu Asp Phe Arg Val
            355                 360                 365

Pro Gly Val Thr Ser Ile Ser Cys Asp Thr His Lys Tyr Gly Phe Ala
            370                 375                 380

Pro Lys Gly Ser Ser Val Ile Met Tyr Arg Asn Ser Asp Leu Arg Met
385                 390                 395                 400

His Gln Tyr Tyr Val Asn Pro Ala Trp Thr Gly Gly Leu Tyr Gly Ser
                405                 410                 415

Pro Thr Leu Ala Gly Ser Arg Pro Gly Ala Ile Val Val Gly Cys Trp
            420                 425                 430

Ala Thr Met Val Asn Met Gly Glu Asn Gly Tyr Ile Glu Ser Cys Gln
            435                 440                 445

Glu Ile Val Gly Ala Ala Met Lys Phe Lys Lys Tyr Ile Gln Glu Asn
450                 455                 460

Ile Pro Asp Leu Asn Ile Met Gly Asn Pro Arg Tyr Ser Val Ile Ser
465                 470                 475                 480

Phe Ser Ser Lys Thr Leu Asn Ile His Glu Leu Ser Asp Arg Leu Ser
                485                 490                 495

Lys Lys Gly Trp His Phe Asn Ala Leu Gln Lys Pro Val Ala Leu His
            500                 505                 510

Met Ala Phe Thr Arg Leu Ser Ala His Val Val Asp Glu Ile Cys Asp
            515                 520                 525

Ile Leu Arg Thr Thr Val Gln Glu Leu Lys Ser Glu Ser Asn Ser Lys
530                 535                 540

Pro Ser Pro Asp Gly Thr Ser Ala Leu Tyr Gly Val Ala Gly Ser Val
545                 550                 555                 560

Lys Thr Ala Gly Val Ala Asp Lys Leu Ile Val Gly Phe Leu Asp Ala
                565                 570                 575

Leu Tyr Lys Leu Gly Pro Gly Glu Asp Thr Ala Thr Lys
            580                 585

(2) INFORMATION FOR SEQ ID NO: 9:

(i) SEQUENCE CHARACTERISTICS:
        (A) LENGTH: 1467 base pairs
        (B) TYPE: nucleic acid
        (C) STRANDEDNESS: single
        (D) TOPOLOGY: linear (ix) FEATURE:
         (A) NAME/KEY: CDS
         (B) LOCATION: 1..1464

(xi) SEQUENCE DESCRIPTION: SEQ ID NO: 9:

ATG CCT AGC ACA GAC CTT CTG ATG TTG AAG GCC TTT GAG CCC TAC TTA      48
Met Pro Ser Thr Asp Leu Leu Met Leu Lys Ala Phe Glu Pro Tyr Leu
 1               5                  10                  15
```

```
GAG ATT TTG GAA GTA TAC TCC ACA AAA GCC AAG AAT TAT GTA AAT GGA      96
Glu Ile Leu Glu Val Tyr Ser Thr Lys Ala Lys Asn Tyr Val Asn Gly
             20                  25                  30

CAT TGC ACC AAG TAT GAG CCC TGG CAG CTA ATT GCA TGG AGT GTC GTG     144
His Cys Thr Lys Tyr Glu Pro Trp Gln Leu Ile Ala Trp Ser Val Val
         35                  40                  45

TGG ACC CTG CTG ATA GTC TGG GGA TAT GAG TTT GTC TTC CAG CCA GAG     192
Trp Thr Leu Leu Ile Val Trp Gly Tyr Glu Phe Val Phe Gln Pro Glu
     50                  55                  60

AGT TTA TGG TCA AGG TTT AAA AAG AAA TGT TTT AAG CTC ACC AGG AAG     240
Ser Leu Trp Ser Arg Phe Lys Lys Lys Cys Phe Lys Leu Thr Arg Lys
 65                  70                  75                  80

ATG CCC ATT ATT GGT CGT AAG ATT CAA GAC AAG TTG AAC AAG ACC AAG     288
Met Pro Ile Ile Gly Arg Lys Ile Gln Asp Lys Leu Asn Lys Thr Lys
                 85                  90                  95

GAT GAT ATT AGC AAG AAC ATG TCA TTC CTG AAA GTG GAC AAA GAG TAT     336
Asp Asp Ile Ser Lys Asn Met Ser Phe Leu Lys Val Asp Lys Glu Tyr
             100                 105                 110

GTG AAA GCT TTA CCC TCC CAG GGT CTG AGC TCA TCT GCT GTT TTG GAG     384
Val Lys Ala Leu Pro Ser Gln Gly Leu Ser Ser Ser Ala Val Leu Glu
         115                 120                 125

AAA CTT AAG GAG TAC AGC TCT ATG GAC GCC TTC TGG CAA GAG GGG AGA     432
Lys Leu Lys Glu Tyr Ser Ser Met Asp Ala Phe Trp Gln Glu Gly Arg
     130                 135                 140

GCC TCT GGA ACA GTG TAC AGT GGG GAG GAG AAG CTC ACT GAG CTC CTT     480
Ala Ser Gly Thr Val Tyr Ser Gly Glu Glu Lys Leu Thr Glu Leu Leu
145                 150                 155                 160

GTG AAG GCT TAT GGA GAT TTT GCA TGG AGT AAC CCC CTG CAT CCA GAT     528
Val Lys Ala Tyr Gly Asp Phe Ala Trp Ser Asn Pro Leu His Pro Asp
                 165                 170                 175

ATC TTC CCA GGA CTA CGC AAG ATA GAG GCA GAA ATT GTG AGG ATA GCT     576
Ile Phe Pro Gly Leu Arg Lys Ile Glu Ala Glu Ile Val Arg Ile Ala
             180                 185                 190

TGT TCC CTG TTC AAT GGG GGA CCA GAT TCG TGT GGA TGT GTG ACT TCT     624
Cys Ser Leu Phe Asn Gly Gly Pro Asp Ser Cys Gly Cys Val Thr Ser
         195                 200                 205

GGG GGA ACA GAA AGC ATA CTC ATG GCC TGC AAA GCA TGT CGG GAT CTG     672
Gly Gly Thr Glu Ser Ile Leu Met Ala Cys Lys Ala Cys Arg Asp Leu
     210                 215                 220

GCC TTT GAG AAG GGG ATC AAA ACT CCA GAA ATT GTG GCT CCC CAA AGT     720
Ala Phe Glu Lys Gly Ile Lys Thr Pro Glu Ile Val Ala Pro Gln Ser
225                 230                 235                 240

GCC CAT GCT GCA TTT AAC AAA GCA GCC AGT TAC TTT GGG ATG AAG ATT     768
Ala His Ala Ala Phe Asn Lys Ala Ala Ser Tyr Phe Gly Met Lys Ile
                 245                 250                 255

GTG CGG GTC CCA TTG ACG AAG ATG ATG GAG GTG GAT GTG AGG GCA ATG     816
Val Arg Val Pro Leu Thr Lys Met Met Glu Val Asp Val Arg Ala Met
             260                 265                 270

AGA AGA GCT ATC TCC AGG AAC ACT GCC ATG CTC GTC TGT TCT ACC CCA     864
Arg Arg Ala Ile Ser Arg Asn Thr Ala Met Leu Val Cys Ser Thr Pro
         275                 280                 285

CAG TTT CCT CAT GGT GTA ATA GAT CCT GTC CCT GAA GTG GCC AAG CTG     912
Gln Phe Pro His Gly Val Ile Asp Pro Val Pro Glu Val Ala Lys Leu
     290                 295                 300

GCT GTC AAA TAC AAA ATA CCC CTT CAT GTC GAC GCT TGT CTG GGA GGC     960
Ala Val Lys Tyr Lys Ile Pro Leu His Val Asp Ala Cys Leu Gly Gly
305                 310                 315                 320

TTC CTC ATC GTC TTT ATG GAG AAA GCA GGA TAC CCA CTG GAG CAC CCA    1008
Phe Leu Ile Val Phe Met Glu Lys Ala Gly Tyr Pro Leu Glu His Pro
                 325                 330                 335
```

```
TTT GAT TTC CGG GTG AAA GGT GTA ACC AGC ATT TCA GCT GAC ACC CAT        1056
Phe Asp Phe Arg Val Lys Gly Val Thr Ser Ile Ser Ala Asp Thr His
            340                 345                 350

AAG CTG GAA AAT ATC AAA GGC ATC TTT GTT TTT GGG AAT CCC CAA TTG        1104
Lys Leu Glu Asn Ile Lys Gly Ile Phe Val Phe Gly Asn Pro Gln Leu
                355                 360                 365

TCA CTC ATT GCT CTG GGA TCC CGT GAT TTT GAC ATC TAC CGA CTA TCA        1152
Ser Leu Ile Ala Leu Gly Ser Arg Asp Phe Asp Ile Tyr Arg Leu Ser
370                 375                 380

AAC CTG ATG ACT GCT AAG GGG TGG AAC TTG AAC CAG TTG CAG TTC CCA        1200
Asn Leu Met Thr Ala Lys Gly Trp Asn Leu Asn Gln Leu Gln Phe Pro
385                 390                 395                 400

CCC AGT ATT CAT TTC TGC ATC ACA TTA CTA CAC GCC CGG AAA CGA GTA        1248
Pro Ser Ile His Phe Cys Ile Thr Leu Leu His Ala Arg Lys Arg Val
                405                 410                 415

GCT ATA CAA TTC CTA AAG GAC ATT CGA GAA TCT GTC ACT CAA ATC ATG        1296
Ala Ile Gln Phe Leu Lys Asp Ile Arg Glu Ser Val Thr Gln Ile Met
                420                 425                 430

AAG AAT CCT AAA GCG AAG ACC ACA GGA ATG GGT GCC ATC TAT GCC ATG        1344
Lys Asn Pro Lys Ala Lys Thr Thr Gly Met Gly Ala Ile Tyr Ala Met
            435                 440                 445

GCC CAG ACA ACT GTT GAC AGG AAT ATG GTT GCA GAA TTG TCC TCA GTC        1392
Ala Gln Thr Thr Val Asp Arg Asn Met Val Ala Glu Leu Ser Ser Val
450                 455                 460

TTC TTG GAC AGC TTG TAC AGC ACC GAC ACT GTC ACC CAG GGC AGC CAG        1440
Phe Leu Asp Ser Leu Tyr Ser Thr Asp Thr Val Thr Gln Gly Ser Gln
465                 470                 475                 480

ATG AAT GGT TCT CCA AAA CCC CAC TGA                                    1467
Met Asn Gly Ser Pro Lys Pro His
            485
```

(2) INFORMATION FOR SEQ ID NO: 10:

(i) SEQUENCE CHARACTERISTICS:
        (A) LENGTH: 488 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Pro Ser Thr Asp Leu Leu Met Leu Lys Ala Phe Glu Pro Tyr Leu
1               5                   10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60

Ser Leu Trp Ser Arg Phe Lys Lys Cys Phe Lys Leu Thr Arg Lys
65                  70                  75                  80

Met Pro Ile Ile Gly Arg Lys Ile Gln Asp Lys Leu Asn Lys Thr Lys
                85                  90                  95

Asp Asp Ile Ser Lys Asn Met Ser Phe Leu Lys Val Asp Lys Glu Tyr
            100                 105                 110
```

-continued

```
Val Lys Ala Leu Pro Ser Gln Gly Leu Ser Ser Ala Val Leu Glu
        115                 120                 125
Lys Leu Lys Glu Tyr Ser Ser Met Asp Ala Phe Trp Gln Glu Gly Arg
130                 135                 140
Ala Ser Gly Thr Val Tyr Ser Gly Glu Glu Lys Leu Thr Glu Leu Leu
145                 150                 155                 160
Val Lys Ala Tyr Gly Asp Phe Ala Trp Ser Asn Pro Leu His Pro Asp
                165                 170                 175
Ile Phe Pro Gly Leu Arg Lys Ile Glu Ala Glu Ile Val Arg Ile Ala
                180                 185                 190
Cys Ser Leu Phe Asn Gly Gly Pro Asp Ser Cys Gly Cys Val Thr Ser
            195                 200                 205
Gly Gly Thr Glu Ser Ile Leu Met Ala Cys Lys Ala Cys Arg Asp Leu
        210                 215                 220
Ala Phe Glu Lys Gly Ile Lys Thr Pro Glu Ile Val Ala Pro Gln Ser
225                 230                 235                 240
Ala His Ala Ala Phe Asn Lys Ala Ala Ser Tyr Phe Gly Met Lys Ile
                245                 250                 255
Val Arg Val Pro Leu Thr Lys Met Met Glu Val Asp Val Arg Ala Met
                260                 265                 270
Arg Arg Ala Ile Ser Arg Asn Thr Ala Met Leu Val Cys Ser Thr Pro
            275                 280                 285
Gln Phe Pro His Gly Val Ile Asp Pro Val Pro Glu Val Ala Lys Leu
        290                 295                 300
Ala Val Lys Tyr Lys Ile Pro Leu His Val Asp Ala Cys Leu Gly Gly
305                 310                 315                 320
Phe Leu Ile Val Phe Met Glu Lys Ala Gly Tyr Pro Leu Glu His Pro
                325                 330                 335
Phe Asp Phe Arg Val Lys Gly Val Thr Ser Ile Ser Ala Asp Thr His
                340                 345                 350
Lys Leu Glu Asn Ile Lys Gly Ile Phe Val Phe Gly Asn Pro Gln Leu
            355                 360                 365
Ser Leu Ile Ala Leu Gly Ser Arg Asp Phe Asp Ile Tyr Arg Leu Ser
        370                 375                 380
Asn Leu Met Thr Ala Lys Gly Trp Asn Leu Asn Gln Leu Gln Phe Pro
385                 390                 395                 400
Pro Ser Ile His Phe Cys Ile Thr Leu Leu His Ala Arg Lys Arg Val
                405                 410                 415
Ala Ile Gln Phe Leu Lys Asp Ile Arg Glu Ser Val Thr Gln Ile Met
                420                 425                 430
Lys Asn Pro Lys Ala Lys Thr Thr Gly Met Gly Ala Ile Tyr Ala Met
            435                 440                 445
Ala Gln Thr Thr Val Asp Arg Asn Met Val Ala Glu Leu Ser Ser Val
        450                 455                 460
Phe Leu Asp Ser Leu Tyr Ser Thr Asp Thr Val Thr Gln Gly Ser Gln
465                 470                 475                 480
Met Asn Gly Ser Pro Lys Pro His
                485
```